United States Patent
Zhou et al.

(10) Patent No.: US 10,182,791 B2
(45) Date of Patent: Jan. 22, 2019

(54) INTEGRATED ULTRASOUND, OCT, PA AND/OR FLORESCENCE IMAGING ENDOSCOPE FOR DIAGNOSING CANCERS IN GASTROINTESTINAL, RESPIRATORY, AND UROGENITAL TRACTS

(71) Applicants: The Regents of the University of California, Oakland, CA (US); University of Southern California, Los Angeles, CA (US)

(72) Inventors: Qifa Zhou, Arcadia, CA (US); Xiang Li, Los Angeles, CA (US); Jacques Van Dam, Los Angeles, CA (US); K. Kirk Shung, Monterey Park, CA (US); Thomas Cummins, Manhattan Beach, CA (US); Zhongping Chen, Irvine, CA (US); Jiawen Li, Irvine, CA (US); Teng Ma, Los Angeles, CA (US)

(73) Assignees: The Regents of the University of California, Oakland, CA (US); University of Southern California, Los Angeles, CA (US)

(*) Notice: Subject to any disclaimer, the term of this patent is extended or adjusted under 35 U.S.C. 154(b) by 271 days.

(21) Appl. No.: 15/027,538

(22) PCT Filed: Oct. 7, 2014

(86) PCT No.: PCT/US2014/059485
§ 371 (c)(1),
(2) Date: Apr. 6, 2016

(87) PCT Pub. No.: WO2015/054243
PCT Pub. Date: Apr. 16, 2015

(65) Prior Publication Data
US 2016/0242737 A1   Aug. 25, 2016

Related U.S. Application Data

(60) Provisional application No. 61/887,790, filed on Oct. 7, 2013.

(51) Int. Cl.
*A61B 5/05* (2006.01)
*A61B 8/00* (2006.01)
(Continued)

(52) U.S. Cl.
CPC .......... *A61B 8/4416* (2013.01); *A61B 1/0016* (2013.01); *A61B 1/00082* (2013.01);
(Continued)

(58) Field of Classification Search
CPC . A61B 8/4416; A61B 10/0283; A61B 8/4461; A61B 5/0084; A61B 5/687;
(Continued)

(56) References Cited

U.S. PATENT DOCUMENTS

| 8,172,857 B2 | 5/2012 | Fogel |
| 2003/0088209 A1 | 5/2003 | Chiu |

(Continued)

*Primary Examiner* — Sanjay Cattungal
(74) *Attorney, Agent, or Firm* — Marcus C. Dawes; Daniel L. Dawes

(57) ABSTRACT

A multimodality imaging system including ultrasound, optical coherence tomography (OCT), photoacoustic (PA) imaging, florescence imaging and endoscopic catheter for imaging inside the gastrointestinal tract with real-time automatic image co-registration capability, including: an ultrasound subsystem for imaging; an optical coherence tomography (OCT) subsystem for imaging, a PA microscopy or tomography subsystem for imaging and a florescence imaging subsystem for imaging. An invasive interventional imaging device is included with an instrumentality to take a tissue biopsy from a location visible on the ultrasound subsystem for imaging, on the optical coherence tomography (OCT) subsystem for imaging, photoacoustic (PA) subsystem for (Continued)

imaging and florescence subsystem for imaging. The instrumentality takes a tissue biopsy from a visible location simultaneously with the visualization of the tissue about to be biopsied so that the tissue biopsy location is visualized before, during and after the biopsy.

27 Claims, 14 Drawing Sheets

(51) Int. Cl.
  *A61B 1/05* (2006.01)
  *A61B 8/12* (2006.01)
  *A61B 10/04* (2006.01)
  *A61B 10/02* (2006.01)
  *A61B 1/00* (2006.01)
  *A61B 1/018* (2006.01)
  *A61B 1/04* (2006.01)
  *A61B 1/273* (2006.01)
  *A61B 5/00* (2006.01)
(52) U.S. Cl.
  CPC .............. *A61B 1/018* (2013.01); *A61B 1/041* (2013.01); *A61B 1/043* (2013.01); *A61B 1/05* (2013.01); *A61B 1/2736* (2013.01); *A61B 5/0066* (2013.01); *A61B 5/0071* (2013.01); *A61B 5/0084* (2013.01); *A61B 5/0095* (2013.01); *A61B 5/687* (2013.01); *A61B 5/6853* (2013.01); *A61B 5/6871* (2013.01); *A61B 8/12* (2013.01); *A61B 8/445* (2013.01); *A61B 8/4461* (2013.01); *A61B 10/0233* (2013.01); *A61B 10/0283* (2013.01); *A61B 10/04* (2013.01)

(58) Field of Classification Search
  CPC ... A61B 5/6853; A61B 5/6871; A61B 5/0066; A61B 5/0071; A61B 5/0095; A61B 8/445; A61B 1/041; A61B 1/2736; A61B 1/0016; A61B 1/018; A61B 1/00082; A61B 1/043
  USPC .................................................. 600/437–480
  See application file for complete search history.

(56) References Cited

U.S. PATENT DOCUMENTS

| | | | |
|---|---|---|---|
| 2006/0195014 A1* | 8/2006 | Seibel .................. | A61B 1/0008 600/102 |
| 2008/0177183 A1 | 7/2008 | Courtney | |
| 2010/0168665 A1 | 7/2010 | Skerven | |
| 2011/0098572 A1* | 4/2011 | Chen .................... | A61B 5/0062 600/463 |
| 2011/0182814 A1* | 7/2011 | Kelly .................. | A61K 49/0002 424/9.1 |
| 2011/0190662 A1* | 8/2011 | McWeeney ............ | A61B 10/04 600/567 |
| 2012/0016243 A1 | 1/2012 | Brown et al. | |
| 2012/0022338 A1 | 1/2012 | Subramaniam et al. | |
| 2015/0359594 A1* | 12/2015 | Ben-Oren .............. | A61B 18/24 606/3 |

* cited by examiner

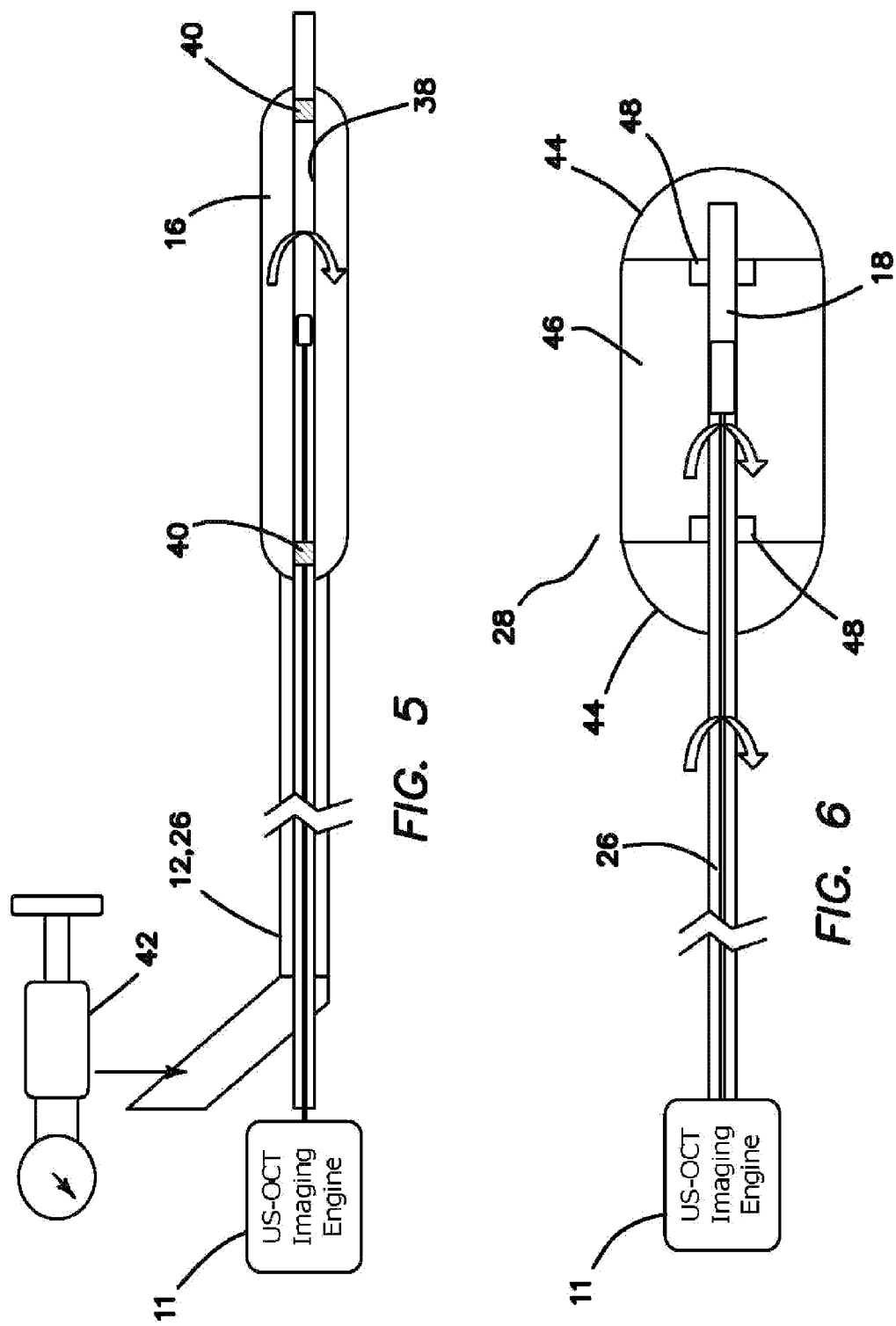

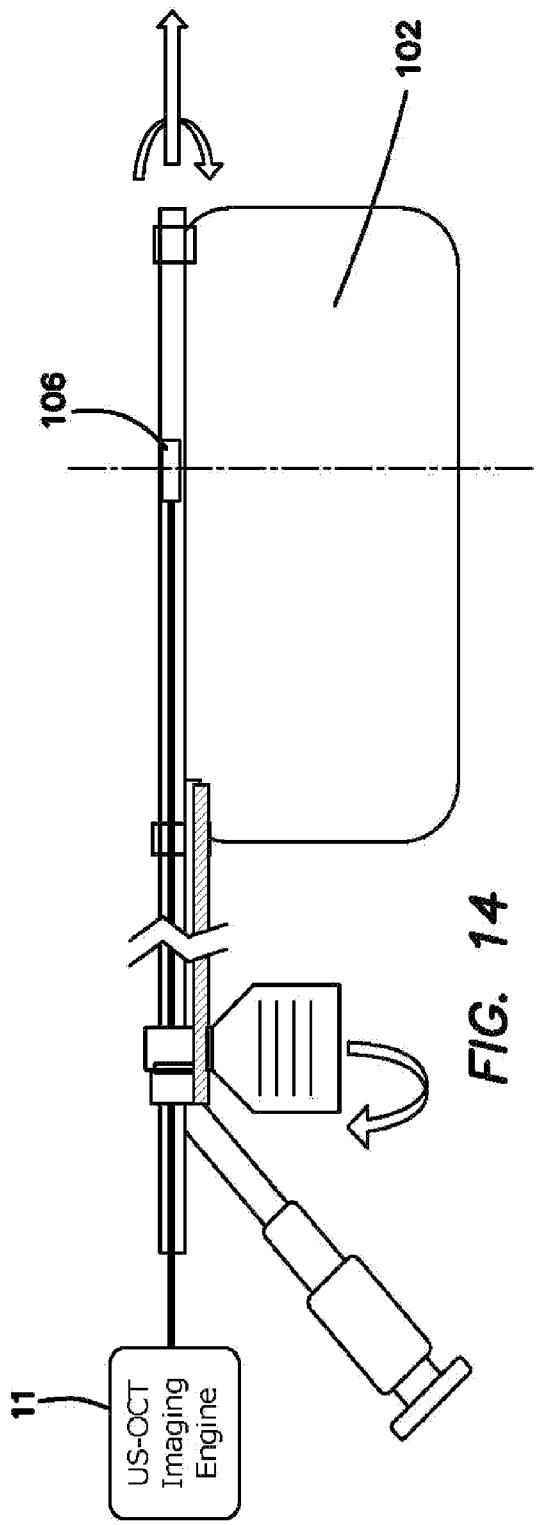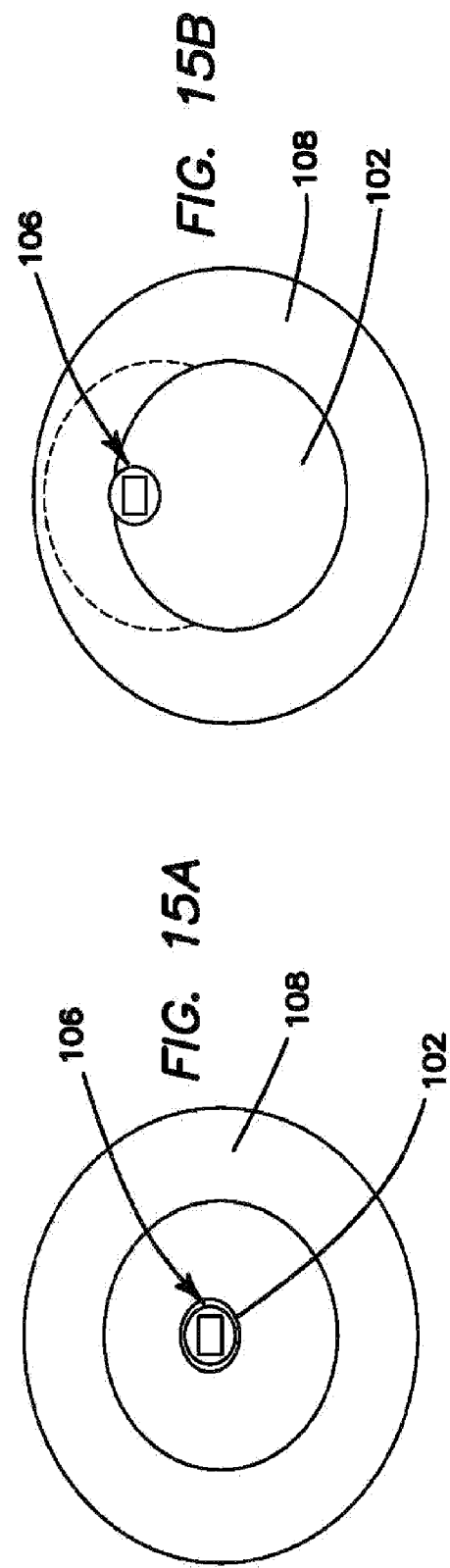

INTEGRATED ULTRASOUND, OCT, PA AND/OR FLORESCENCE IMAGING ENDOSCOPE FOR DIAGNOSING CANCERS IN GASTROINTESTINAL, RESPIRATORY, AND UROGENITAL TRACTS

CROSS-REFERENCE TO RELATED APPLICATIONS

This application claims priority to, and the benefit of the earlier filing date of: US provisional patent application entitled INTEGRATED ULTRASOUND AND OPTICAL COHERENCE TOMOGRAPHY (oct) ENDOSCOPE FOR DIAGNOSING CHOLANGIOCARCINOMA AND CYSTIC NEOPLASMS OF THE PANCREAS filed on Oct. 7, 2013, Ser. No. 61/887,790, pursuant to 35 USC 119, the contents of which are incorporated herein by reference.

GOVERNMENT SUPPORT

This invention was made with government support under contract EB-10090, awarded by the National Institutes of Health. The government has certain rights in the invention.

BACKGROUND

Field of the Technology

The disclosure relates to the field of endoscopic probes using ultrasound and optical coherent tomography.

Description of the Prior Art

Gastrointestinal (gastrointestinal) cancers causes more than 140,000 deaths with more than 290,000 new cases in the United States in 2014. Esophageal cancer is one of most common gastrointestinal cancer diseases with a five-year survival rate only 16%. Esophageal adenocarcinoma is developed from the gastro esophageal reflux disorder of Barrett's esophagus (BE). The unique characteristic of BE is abnormal replacement of squamous epithelium with columnar epithelium. The detection of preceding dysplasia is believed to reduce the risk of adenocarcinoma. Colorectal cancer is another common gastrointestinal disease with high morbidity and mortality rates. Although most colorectal cancers arise from adenomatous polyps that are detectable using conventional endoscopy, many flat (non-polypoid) lesions, up to 50%, are missed during routine examinations.

The standard procedure to facilitate early diagnosis of common gastrointestinal cancer diseases is to perform histological analysis based tissue biopsy in abnormal regions that can be identified by endoscopy, or random biopsies over a large area (such as entire length of BE or colon). Besides inadequate sampling, the problem of early detection of dysplasia in the gut is exacerbated in the presence of chronic inflammatory conditions such as esophagitis, since early-stage lesions are difficult to distinguish from inflamed gastrointestinal mucosa by the endoscopist.

In addition to the most common upper digestive track cancer diagnosis, such as esophagus cancer, one specific clinical problem to be solved is the diagnosis of cholangiocarcinoma (CCA). CCA is an epithelial cancer of bile ducts with features of cholangiocyte differentiation. CCA is the second most common primary hepatic malignancy. The patient incidence in the United States is 1.77/100,000 and this number is increasing in Western countries. Advanced CCA has a devastating prognosis, with a median survival of <24 months. Hepatobiliary malignancies account for 13% of the 7,6 million annual cancer-related deaths worldwide, and CCA accounts for 10% to 20% of the deaths from hepatobiliary malignancies. The market size of diagnosing CCA is around 0.5~1 billion dollars.

The conventional standard for diagnosing CCA is a bile duct biopsy technique, which uses a tiny catheter-based brush to be advanced into the bile duct to scrape the surface of duct wall, in order to harvest cells from the lesion area for cytological analysis. This crude approach is very invasive and harmful to the patients and the accuracy is still below 50%. Moreover, the biopsy approach only allows the clinician to harvest cells on the inner surface of bile duct, and has no diagnosing ability for tissues several millimeters beyond the epithelium of the bile duct. These serious limitations of the current clinical practice for diagnosis of CCA demonstrate a great, need for developing more advanced imaging technologies with higher sensitivity and safety.

Another specific problem to be solved is the diagnosis of cystic neoplasms of the pancreas. Cystic neoplasms of the pancreas include serous cystic tumors, mucinous cystic neoplasms, solid pseudopapillary neoplasms, cystic islet cell tumors, and intraductal papillary mucinous neoplasms of the pancreas (IPMNs). IPMNs have also been referred to as mucinous duct ectasias and intraductal papillary mucinous tumors. IPMNs are potentially malignant intraductal epithelial neoplasms that are grossly visible (>1 cm) and are composed of mucin-producing columnar cells. At this time, many patients undergo surgical resection of pancreatic cysts. Classification and thus prognosis of pancreatic cysts are currently best made at the time of surgical resection as there are yet no imaging characteristics or cyst fluid tumor markers sensitive and specific enough on which to base such decisions. A technology is needed that would provide the physician with a preoperative diagnosis on which to base decisions as the basis of whether to operate or not. This could have a profound clinical as well as economic impact.

BRIEF SUMMARY

The illustrated embodiments of the invention include an integrated ultrasound-optical coherence tomography (OCT) imaging system and endoscopic catheter for imaging inside a bile duct and pancreatic duct to diagnose a cholangiocarcinoma and cystic neoplasm of the pancreas. The medical imaging endoscope is intended for clinical practice. The imaging device includes a multiple-function imaging catheter and an imaging system. During the diagnostic procedure, known as ERCP (endoscopic retrograde cholangiopancreatography), the catheter is advanced either into the bile ducts or pancreas of patients, providing real time cross sectional ultrasound. OCT high resolution imaging of duct walls, photoacoustic imaging and/or florescence imaging with molecular contrasts for the cancerous tissue or abnormal tissue, to diagnose the etiology of stricture/obstruction, vascular compression, tumor staging, and other lesions. As tumors of the bile duct and pancreas have a particularly poor prognosis when detected in their advanced forms, the early diagnosis made possible by the invention has a profound effect on the medical management and outcome of the disease.

In one embodiment the device is a minimally invasive interventional imaging device which includes an instrumentality to take a tissue biopsy from a location that is visible on the imaging system. The device enables the physician to visualize the tissue he or she is about to biopsy with the imaging catheter, and to simultaneously take a tissue biopsy with the same device. The imaging information increases the diagnostic accuracy of tissue biopsy by allowing the physician to first visualize the tissue in the bile duct, which he or she deems suspicious, and then to take a biopsy of that specific target rather than merely scraping cells off only the inner lining of the bile duct without any indication of where a lesion might be.

The illustrated embodiments include an integrated ultrasound-optical coherence tomography (OCT) imaging system and endoscopic catheters for image guided biopsy.

Biopsy area includes all of the human digestive system, including the esophagus, bile duct, stomach, pancreatic duct, Duodenum.

The imaging catheter in one embodiment includes use a tethered capsule based catheter, or balloon based catheter which is delivered by an endoscope or duodenoscope.

The challenge of inserting a catheter through an ERCP endoscope having a sharp turn is solved by a back-to-back probe design, whose rigid components are miniaturized in size or micromotor design, which docs not require a transition or rotation through a sharp turn.

The imaging probe in one embodiment includes is based on a micromotor design or proximal rotation mechanism.

The OCT subprobe includes in one embodiment includes a GRIN-lens based or ball-lens.

The IVUS subprobe in one embodiment includes ring transducer or single element transducer. The material of the transducer is a PMN-PT 1-3 composite or PZT 1-3 composite.

In one embodiment the invention includes photoacoustic (PA) imaging, florescence or elastrography imaging modalities in addition to ultrasound and OCT. The fiber that delivers the OCT optical radiation beam can also be a special fiber, including but not limited to double clad fiber or photonic crystal fiber, which can deliver both fluorescent excitation beam or photoacoustic excitation beam. The laser inducted florescence beam can be collected by the same special fiber for fluorescence imaging. The ultrasonic transducer can receive laser induced photoacoustic signal for generating photoacoustic image in addition to the US image. Therefore, fluorescence and/or photoacoustic imaging can be obtained simultaneously with the OCT and US image. Thus, this invention is able to incorporate ultrasound to provide the deep penetrated far field imaging of the GI tract, OCT to provide high resolution imaging of GI tract, and photoacoustic imaging (photoacoustic microscopy and photoacoustic tomography) to provide molecular contrast to target cancerous or abnormal tissue in GI tract. This multi-modality imaging system can be accomplished in the endoscopic probe design described in this invention. Different biocompatible molecular contrast agents, organic dyes, or nano-particles can be added so as to enhance the molecular contrasts.

The invention in one embodiment includes an asymmetric balloon with the imaging probe inside or outside of balloon or includes a centering balloon, to position the imaging probe directly on the lining of the gastrointestinal tract. The advantages of this embodiment includes both imaging more deeply into the tissue and also making direct access to the tissue for purposes of collecting a tissue biopsy specimen.

The invention in one embodiment includes a vacuum assist to ensure a good seal between the ultrasound transducer and the tissue.

The invention in one embodiment includes a distal tip articulation, guide wire channel or other mechanism to navigate the catheter to area of interest for imaging.

The invention in one embodiment includes a distal end biopsy needle.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 5 is a side cross-sectional view of one embodiment of balloon catheter.

FIG. 6 is a side cross-sectional view of one embodiment of tethered capsule.

FIG. 13a shows the balloon unfilled and FIG. 13b shows the balloon filled.

FIG. 14 is a side cross-sectional view of one embodiment of an imaging probe with an asymmetrical water-filled balloon that is attached to the outside of the imaging probe.

Expanding the water-filled balloon presses the imaging probe against the wall of the gastrointestinal tract.

FIGS. 15a and 15b are front cross-sectional views of one embodiment of an imaging probe with an asymmetrical water-filled balloon that is attached to the outside of the imaging probe. Expanding the water-filled balloon, presses the imaging probe against the wall of the gastrointestinal tract. FIG. 15a shows the balloon unfilled and FIG. 15b shows the balloon filled.

Figure 16:
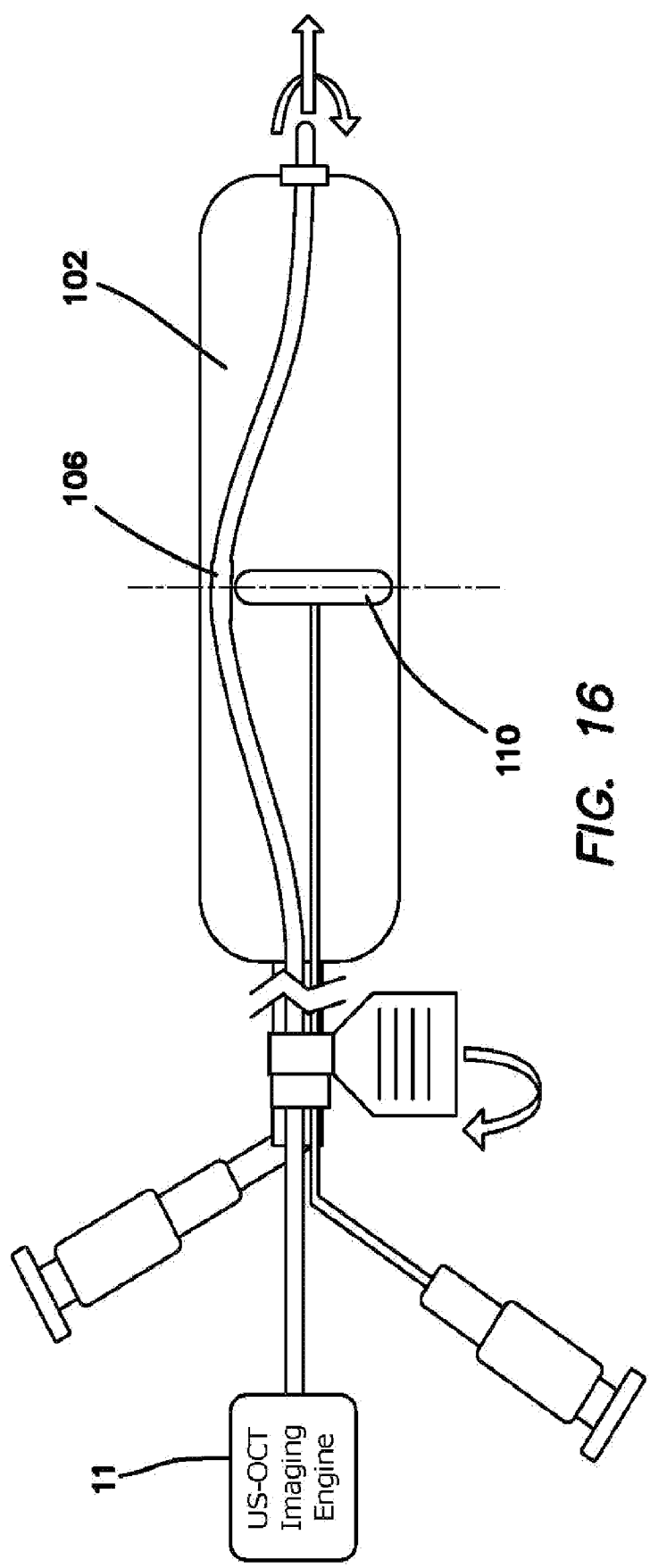

FIG. 16 is a side cross-sectional view of one embodiment of an imaging probe with centering balloon. The centering balloon presses the imaging probe aperture against the inner wall of the water-filled balloon. The probe positioning tab allows the user to rotate the entire-water-filled balloon so as to direct the imaging probe.

Figure 17A:
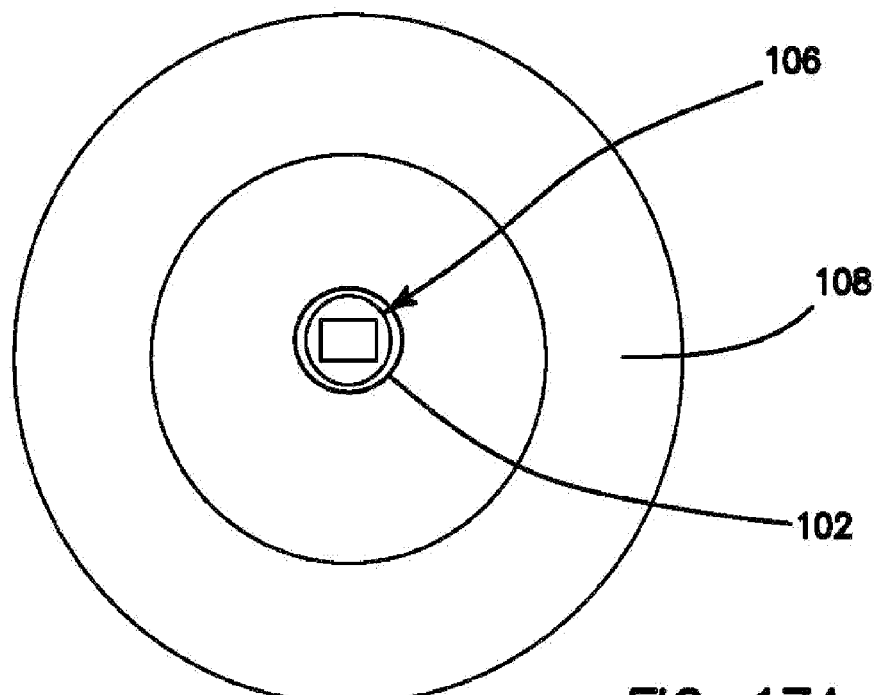
Figure 17B:
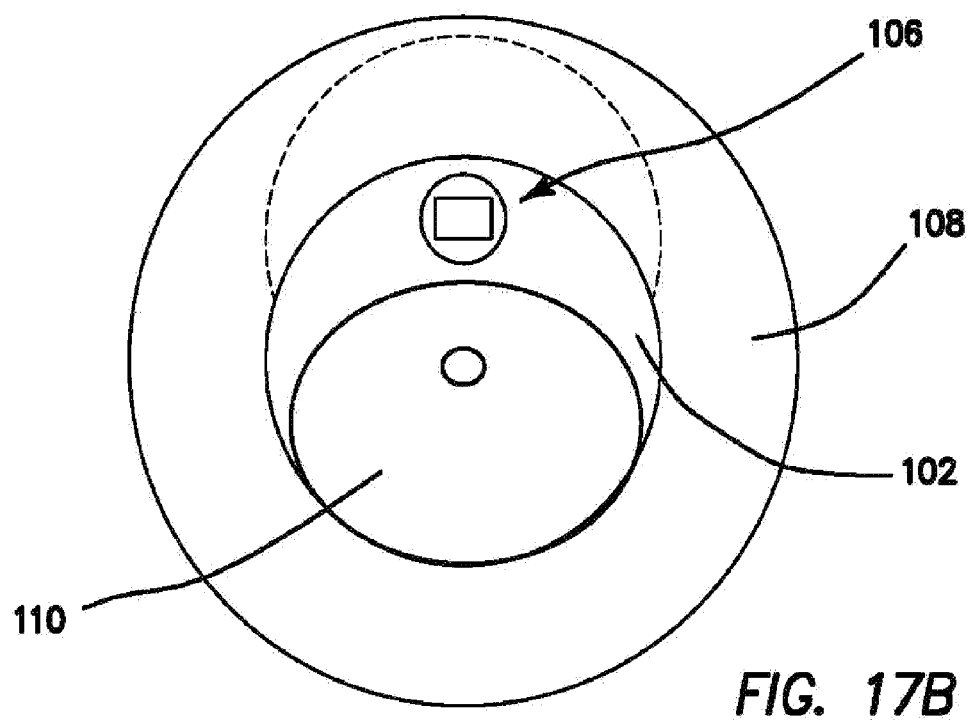

FIGS. 17a and 17b are front cross-sectional views of one embodiment of an imaging probe with centering balloon. The centering balloon presses the imaging probe aperture against the inner wall of the water-filled balloon.

Figure 18A:
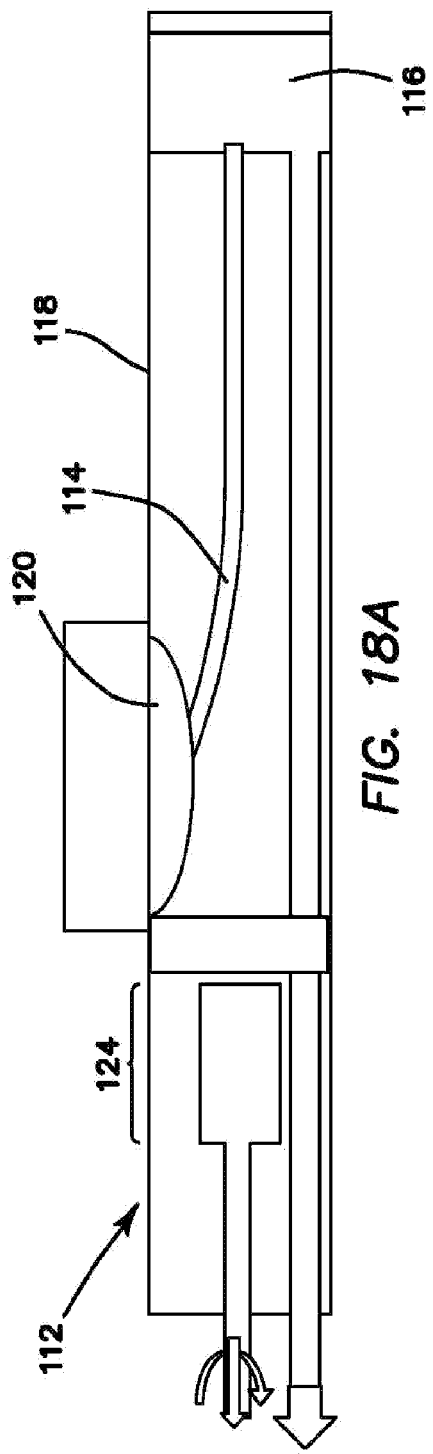
Figure 18B:
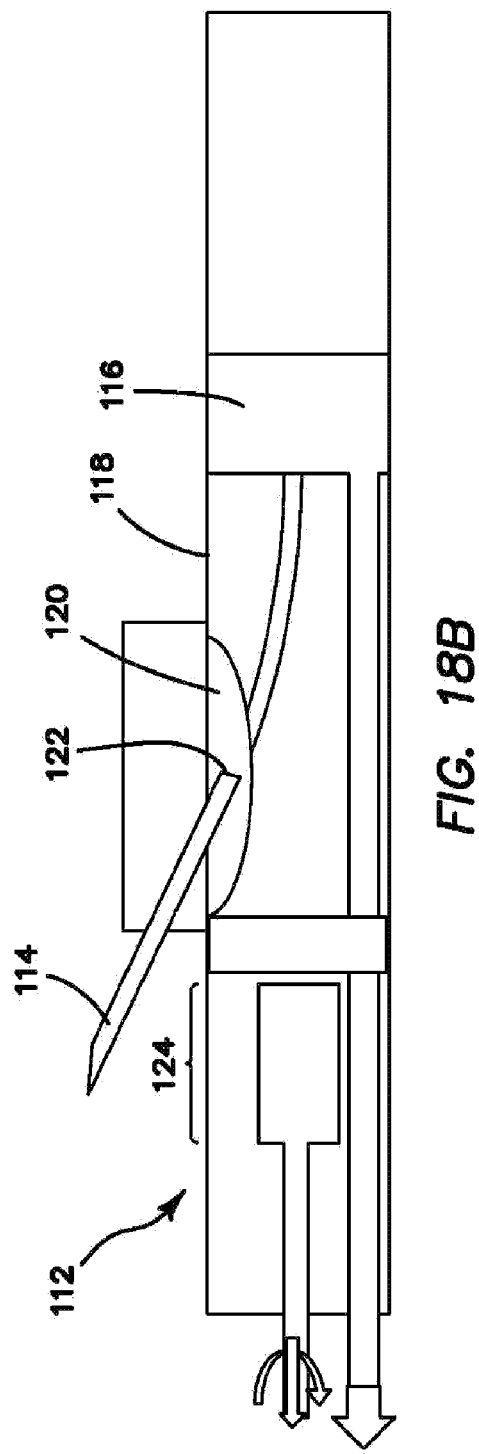

FIGS. 18a and 18b are side cross-sectional views of one embodiment of a tissue biopsy sampling mechanism. A Biopsy trigger cable can be pulled to advance a flexible biopsy needle into the tissue. FIG. 18a shows the biopsy needle undeployed and FIG. 18b shows the biopsy needle deployed.

Figure 19:
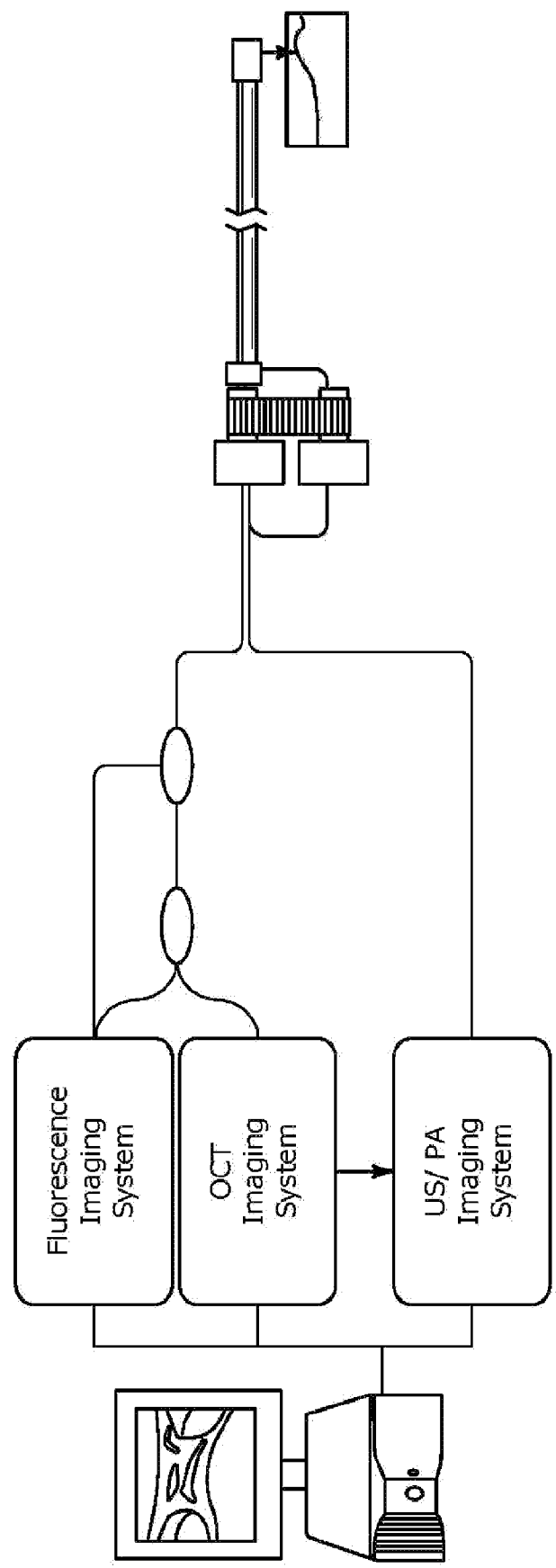

FIG. 19 is schematic of an integrated multimodality system that combines US with OCT/PA/Fluorescence imaging.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Imaging System and Catheter Design

What is illustrated in the various embodiments of the invention includes a device 10 which is a minimally invasive interventional imaging device 10 with the ability to take a tissue biopsy from a location that is visible on the imaging system. The purpose of device 10 is to enable the physician: to visualize the tissue he or she is about to biopsy with the imaging catheter 12, and simultaneously take a tissue biopsy with the same device 10. The additional imaging information increases the diagnostic accuracy of the tissue biopsy by allowing the physician to first visualize the tissue in the bile duct which he or she deems suspicious and then take a biopsy of that, specific target rather than merely scraping cells off only the inner lining of the bile duct without any indication of where a lesion might be.

The imaging system of device 10 integrates at least two or more imaging modalities: an ultrasound, an OCT, a PA and/or a florescence imaging modality. All imaging modalities provide a radial shaped cross sectional view of the bile duct wall in real time. High frequency ultrasound imaging with 10-60 MHz has a penetration depth around 5-20 mm and resolution on the order of 100 μm. OCT imaging is capable of seeing tissue structures with even higher resolution around 10~20 μm, but with a shallower penetration of 2 mm. PA imaging can provide specific molecular contrast, resolution on the order of 10~100 μm and a depth penetration of 0.5~10 mm. Florescence imaging has been used very often to target cancerous cells due to its superior molecular specificity. By using a double cladding fiber and double cladding fiber combiner, a system can simultaneously has both OCT and florescence imaging capability. Either FDA approved florescence dye can be injected or auto-fluoresce technique can be applied.

For the OCT subsystem 11, a long imaging range system is utilized and realized. More than 80% of people have a common bile duct with an inner diameter over 6 mm and the inner diameter of gastrointestinal tract is over 2.5 cm, thus a long image range OCT subsystem 11 is needed for gastrointestinal imaging. One embodiment of long range OCT subsystem 11 is to use a long-coherent-length OCT laser 50 (with a coherent length of over 30 mm, such as Santec MEMS laser or Thorlabs VCSEL laser). Another embodiment of a long range OCT system 11 includes using the design of the previous patent (US20110009752 A1 "Endoscopic long range Fourier domain optical coherence tomography (lr-fd-oct)") Other embodiments of long range OCT subsystems 11 include polarization based demodulation, acoustic-optics frequency shift, or phase modulation to detect a complex OCT signal.

In the illustrated embodiment the imaging catheter 12 integrates two imaging modalities: an ultrasound and OCT modality. By integrating those modalities, the catheter 12 provides complimentary information in terms of resolution and penetration. The overall size of the catheter 12 is around 2.0 mm in diameter, which is safe and feasible to be advanced through the accessory channel of an endoscope 14 and into the sections of the bile ducts with strictures. Moreover, the applications of the microcatheter 12 can be easily expanded into other organs such as the pancreas as well as other parts of the gastrointestinal tract.

Figure 1:
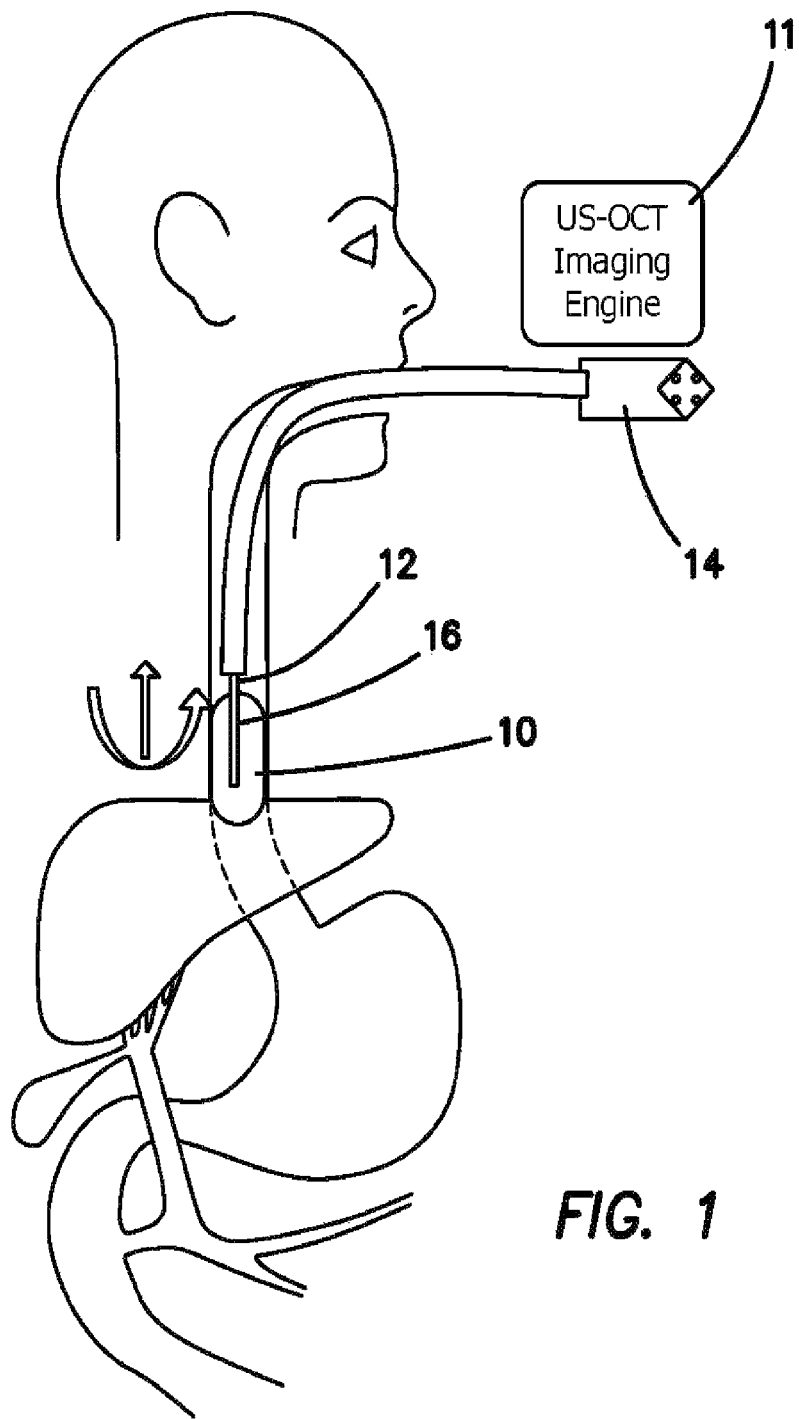
FIG. 1 is a diagram which illustrates the procedures of dual-modality upper gastrointestinal tract imaging by using the balloon based US+OCT catheter in coordinate with the forward-looking video endoscope.

FIG. 1 illustrates the procedures of dual-modality upper gastrointestinal tract imaging by using the balloon based US+OCT catheter 12 in coordinate, with the forward-looking video endoscope 14. The forward-looking endoscope 14 is inserted into the patent's tipper gastrointestinal tract, such as esophagus 15 shown in FIG. 1, to facilitate the general examination. For the suspicious disease region, the endoscope is pulled back at certain length and then the US+OCT/PA/florescence imaging catheter 12 is then inserted through the accessory channel of the endoscope 14, whose imaging region is large enough to cover the pull-back length of the endoscope 14. A US-OCT imaging engine 11 is coupled to or communicated with catheter 12, which provides the ultrasound and optically coherent tomographic probing and measuring signals and image rendering circuitry. The balloon 16, which is transparent to ultrasound and optical light beam, is inflated by the low pressure pump (not shown) to get full contact with, the gastrointestinal tissue. The catheter 12 then rotates within a central imaging sheath 18, which transparent to ultrasound and optical light beam, to facilitate the cross-sectional imaging of the gastrointestinal tract. Three dimensional imaging is achieved during the pull-back scanning of the catheter 12 within the imaging sheath 18 like the one shown in FIG. 6.

Figure 2:
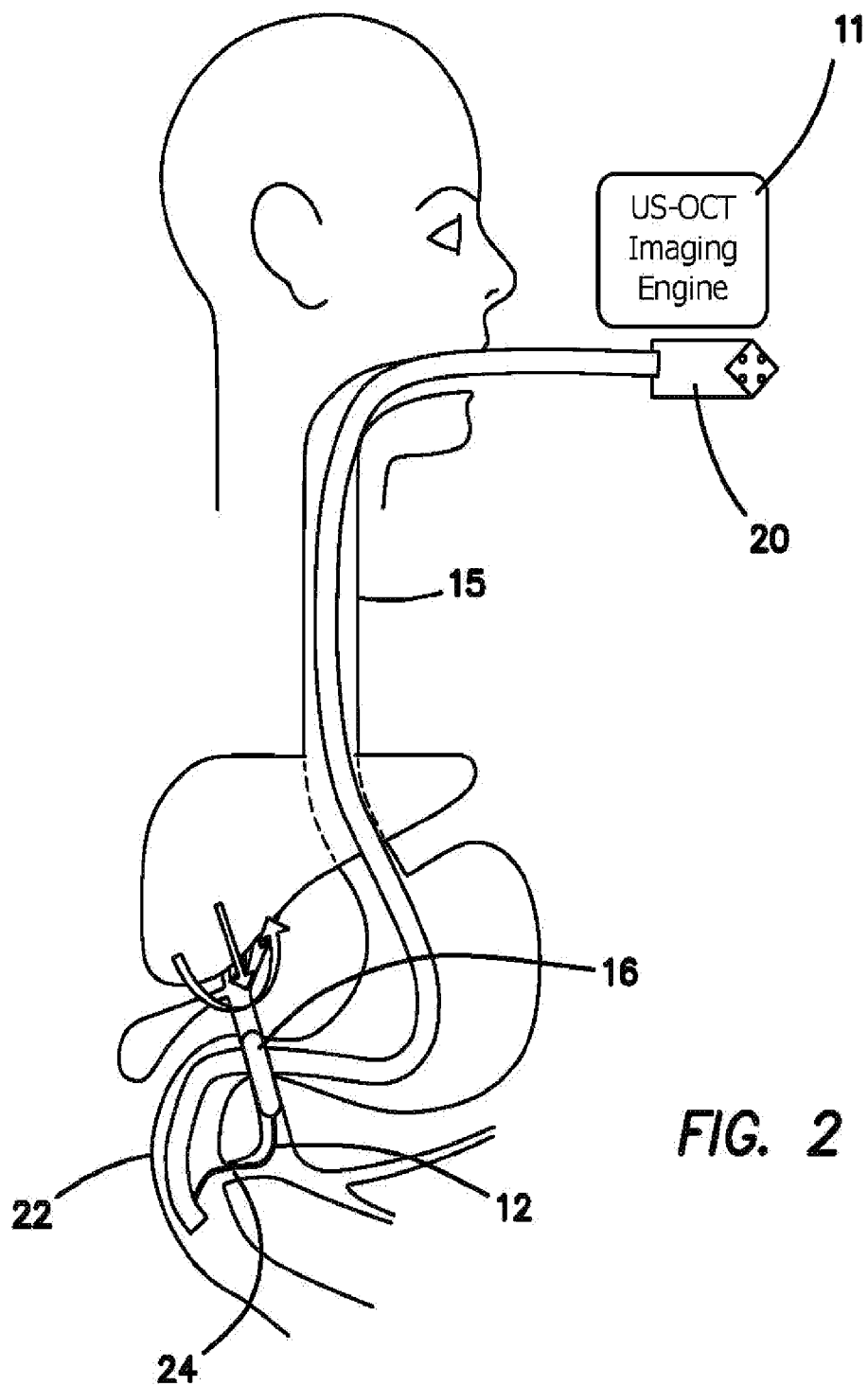
FIG. 2 is a diagram which illustrates the procedures of dual-modality bile/pancreatic duct imaging by using the balloon based US+OCT catheter in coordinate with the side-looking video duodenoscope in the ERCP.

FIG. 2 illustrates the procedures of dual-modality bile/pancreatic duct imaging by using the balloon based U+OCT/PA/florescence catheter 12 in coordination with a side-looking video duodenoscope 20 in the ERCP. The duodenoscope 20 is inserted into the duodenum 22 of patient, and the entrance of the papilla 24 can be observed. The guidewire (not shown), associated with or guiding the balloon-based US+OCT/PA/florescence catheter 12, is then entered into the papilla 24 through the accessory channel of the duodenoscope 20 with a selected elevation, angle that is adjusted at the tip of duodenoscope 20. Cross-sectional imaging and three dimensional imaging is achieved by a rotational pull-back scanning mechanism after the balloon 16 is inflated.

Figure 3:
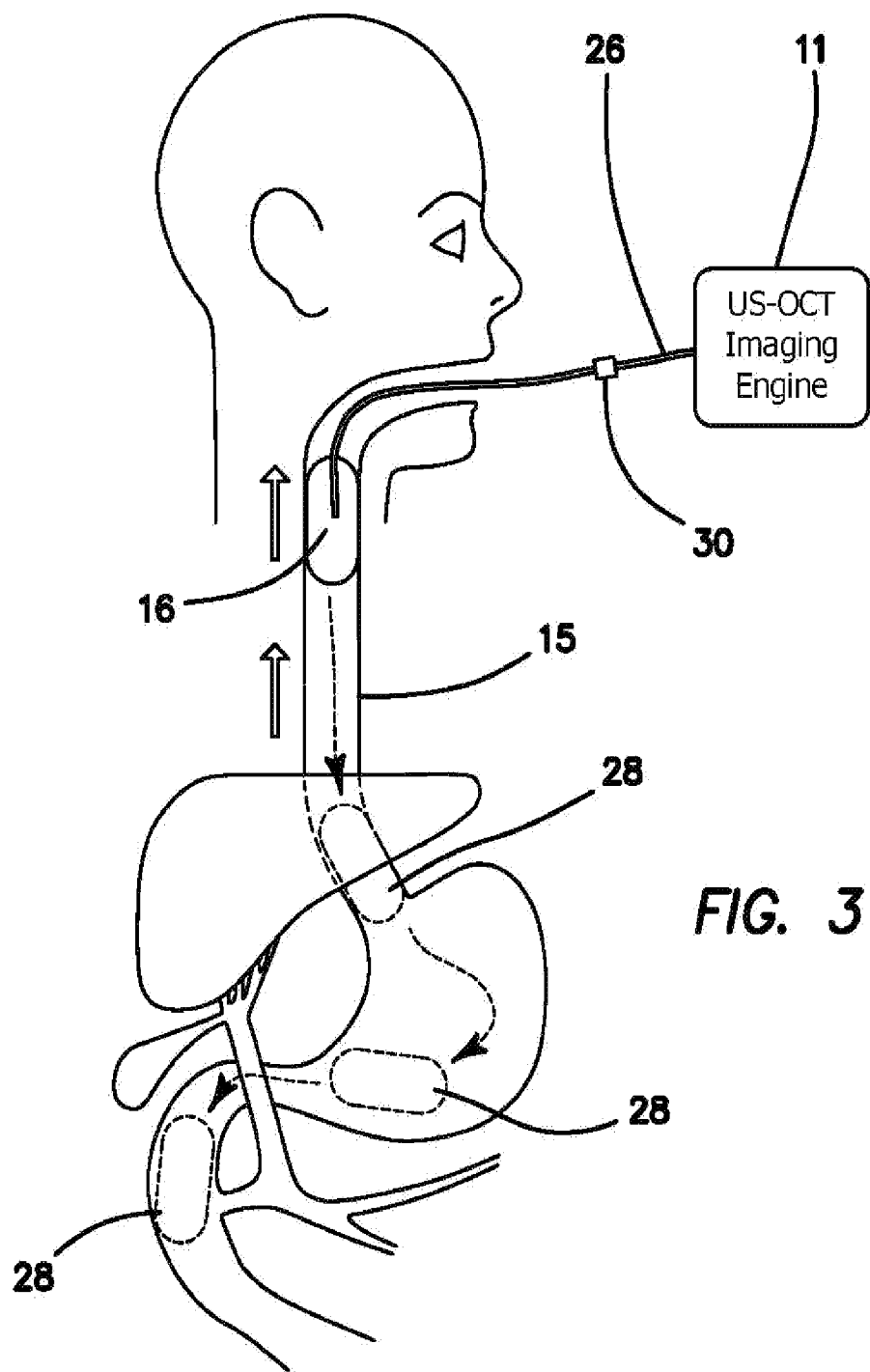
FIG. 3 is a diagram which illustrates the procedures of dual-modality upper gastrointestinal tract imaging by using capsule based US+OCT probe.

FIG. 3 illustrates the procedures of dual-modality upper gastrointestinal, tract imaging using a capsule based US+OCT/PA/florescence probe or tether 26. The capsule 28 is swallowed together with a sip of water. The imaging procedure begins when the capsule 28 starts to descend though the esophagus 15. US+OCT/PA/florescence tether 26 remains connected to capsule 28 as it descends. A marker 30 on the tether 26 exterior to the patient is able to record the distance that the capsule 28 has traveled. A more accurate three dimensional imaging of the tissue than achievable during descent can be achieved by using a fixed pull-back speed applied to the capsule 28 during the imaging process.

Figure 4:
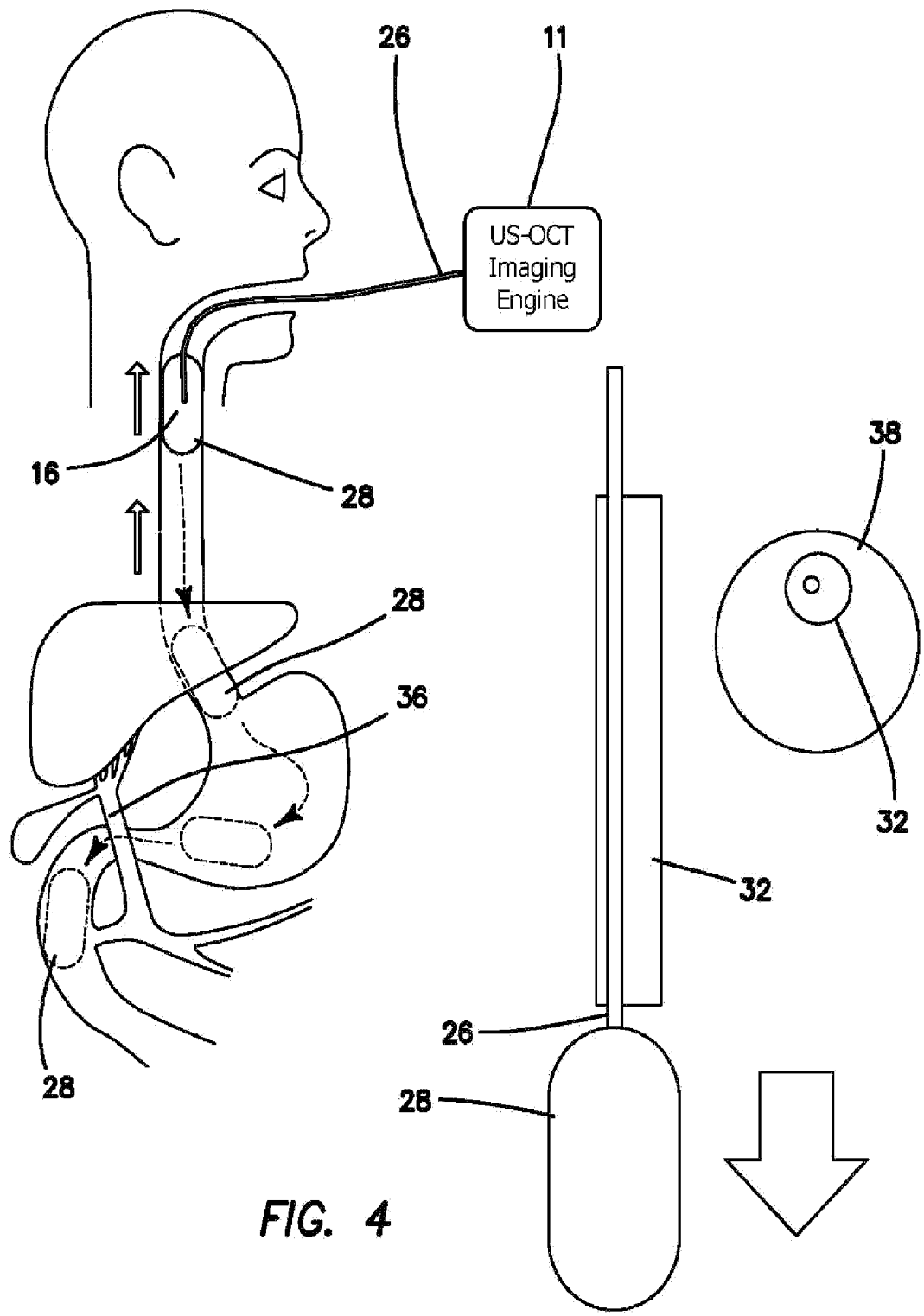
FIG. 4 is a diagram which illustrates another embodiment of the mechanism to inserting capsule as shown in the right side portion of the drawing.

FIG. 4 illustrates the procedures of dual-modality upper gastrointestinal tract imaging by using capsule based US+OCT/PA/florescence probe or tether 26 coupled to or communicated to US-OCT/PA/florescence imaging engine 11 including an advancing sheath 32 as shown in enlarged scale-in the right portion of the drawing, which is used to push the capsule 28 further into the gastrointestinal tract. As depicted in the perpendicular cross sectional view in the insert in the drawing advancing sheath 32 has a capsule tether slot 34 defined longitudinally through, it to accommodate tether 26. By applying tension to the tether 26 the capsule 28 is pulled upwards through the esophagus and captures imaging data necessary for 3D reconstruction.

FIG. 5 illustrates the side cross-sectional view of one embodiment of balloon catheter 12, 26 which is inserted into the accessory channel of the endoscope 14 or duodenoscope 20 in order to perform the dual-modality imaging of gastrointestinal tract such as esophagus 15 and bile ducts 36. During the imaging experiments, saline or PBS is injected into the balloon 16 through a low pressure inflator 42 for inflating balloon 16. The balloon 16 contains a central lumen sheath 38 also filled with PBS to facilitate the rotational scanning mechanism for the cross-sectional imaging and pull-back mechanism for three dimensional imaging. Two radiopaque markers 40 are placed at the proximal and distal end of the balloon 16, which are tracked under the fluoroscopy. The whole size of the balloon 16 is less than 3 mm in diameter before inflating, which can be fit in the accessory channels of most, commercial endoscopes 14. Various embodiments, or designs of US-OCT probe 12, 26 can be used to perform imaging.

FIG. 6 shows the tethered capsule based imaging catheter 26 that can be used to image the esophagus, small intestine or other gastrointestinal tract tissue without the guidance of the endoscope 14. The capsule 28 has a length of 25-30 mm and width of 10-15 mm. The capsule 28 comprises two hollow hemispherical caps 44 and a thin layer cylindrical shell 46, which is transparent to ultrasound and OCT/PA/florescence light beam, in the middle filled with water in order to provide an efficient but transparent ultrasound coupling into the adjacent tissue. An imaging sheath 18 extends into or through the capsule 28, axially centered therein by washers 48, to hold the rotatable scanning catheter 26 to facilitate the cross-sectional imaging and to serve as the tether for three dimensional imaging of the digestive tract, when catheter 26 and the imagining sensors are pulled back inside the sheath 18 or when the entire capsule 28 is moved forward or back in the body channel. Sheath 18 is transparent or at least partially transparent to the ultrasound and optical OCT/PA/florescence signals, or has a window defined therein to allow signal passage. It may be necessary to push the tethered capsule 28 down into the esophagus, the stomach or the small intestine with a stiffer advancing sheath 32 since the tether 26 cannot exert a pushing force due to its thin and pliable construction. One use of the tethered capsule 28 is to advance the capsule 28 with the sheath 18 until it is located just distally to the region to be imaged. Then the pullback motor (not shown) engages tether 26 and pulls the capsule 28 upward or back towards the mouth, capturing image data as it moves.

Figure 7A:
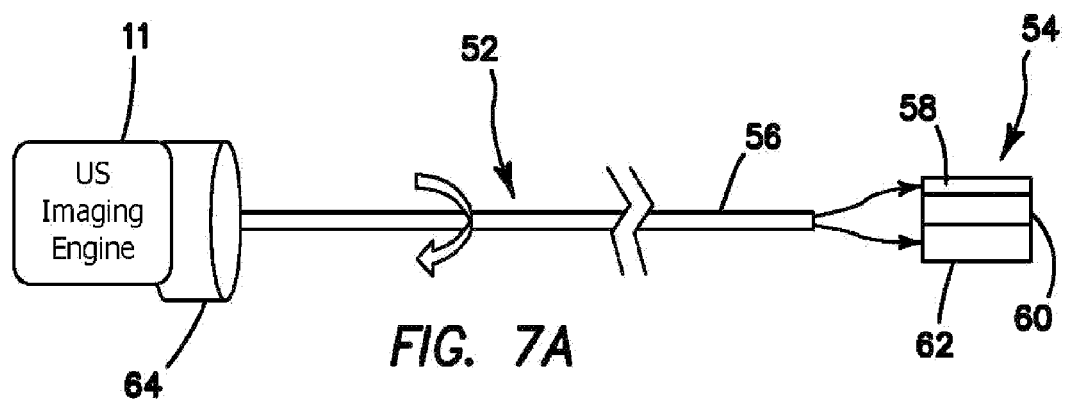
FIG. 7a is a diagram of an embodiment of US sub-probe and FIG. 7b is a schematic, diagram of 1-3 composite material.
Figure 7B:
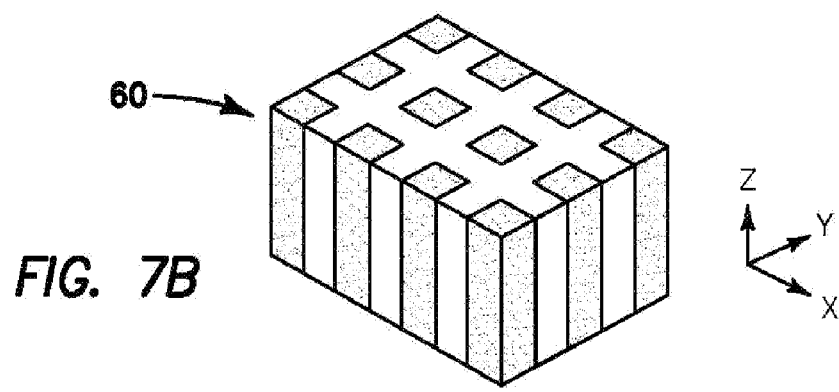

FIG. 7a illustrates an embodiment of an ultrasound (US) subprobe 52 using a transducer 54 with a complex (1−x) [Pb(Mg$_{1,2, \text{ or } 3}$)O$_3$]−x[PbTiO$_3$](PMN-PT) single crystal or PMN-PT single crystal/epoxy material or Pb[Zr$_x$Ti$_{1−x}$]O$_3$ (PZT) ceramics or PZT ceramics/epoxy material as shown in FIG. 7b. The functional element 60 of the transducer 54 can be lapped to a thickness of 300 µm or less before it is mechanically diced into 0.4 mm*0.4 mm square shape. The center frequency of the ultrasonic transducer 54 varies from 10 MHz to 60 MHz with the respective thickness of the functional or piezoelectric layer 60, which in turn adjusts the resolution and depth penetration of ultrasonic images. The center core of a coaxial cable 56 is connected to the backing layer or back electrode 62 and covered by epoxy to insulate it from the front or surface electrode 58 without increasing the thickness of the transducer 54. The ground wire is connected to the surface electrode 58 of the transducer 54. The central wire and ground wire of the coaxial cable 56 are connected at their proximal end to a slip ring 64 to allow rotational scanning. FIG. 7b illustrates the design of PMN-PT 1-3 composite material and PZT 1-3 composite with alternating arrangement of piezoelectric material and epoxy by using either dice-and-fill or micromachined dry-etching methods. Excellent properties of this single element transducers are achieved by the improved electromechanical coupling coefficient (kt~0.9) where kt is the laterally clamped, thickness-dilatational coupling factor, high piezoelectric coefficient (d33~800 pm/V), where d is and lower acoustic impedance (Z~20 Mrayl).

Figure 8A:
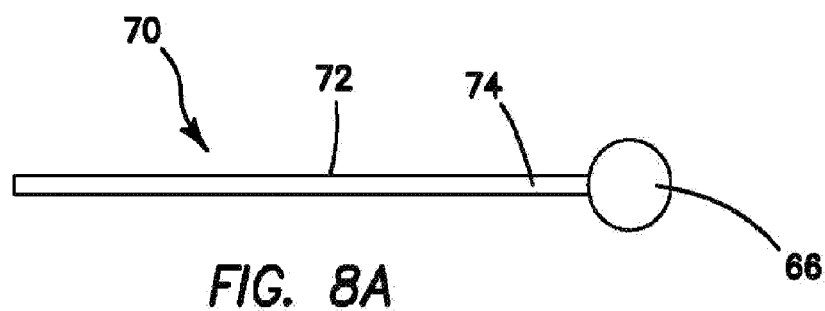
FIG. 8a is a diagram of an embodiment of OCT ball lens and FIG. 8b is a diagram of the GRIN lens designs. The focal, length of this bait lens can be adjust by changing the length of coreless fiber and size of the ball lens.
Figure 8B:
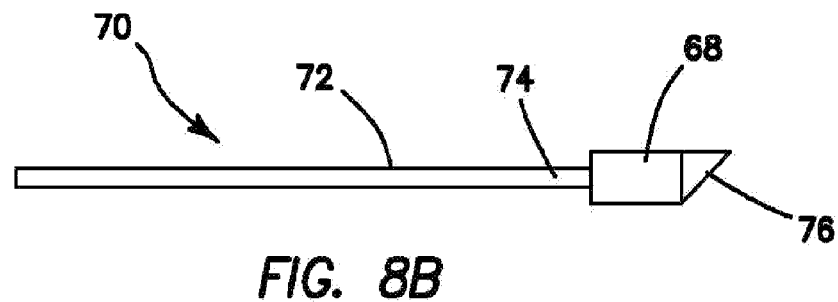

FIGS. 8a and 8b illustrate an embodiment including an OCT ball lens 66 and traditional GRIN lens 68. For the OCT subprobe 70, we can choose a ball-lens design or GRIN lens design using a distal side reflecting prism 76. For mass production, we prefer a ball-lens design of FIG. 8a, which has the potential to be manufactured in large quantities while maintaining a constant performance. It also enables less insertion loss and stronger interfaces than, the traditional GRIN lens design of FIG. 8b. A single mode fiber 72 is fusion-spliced to a fiber spacer 74 using a splicing workstation. Then, a ball lens 66 with a fiber spacer 74 is created at the distal end of the fiber spacer 74 using the splicing workstation. Ball lens 66 can generate a beam focusing at ~3 mm from the ball's surface, which is suitable for gastrointestinal system imaging. Next, the surface 67 of lens 66 is mechanically polished until total internal reflection (TIR) occurs at the polished surface 67 of lens 66. The ball lens 66 is later inserted into a seated polyimide tube 81, isolating the ball lens 66 from the water in the sheath 83 and maintaining an air-fiber interface to ensure that total internal reflection (TIR) occurs at the polished surface of lens 66.

In the case of IVUS+OCT+fluroscence imaging, a double cladding fiber will be used to replace the single mode fiber 72. For IVUS+OCT+PA imaging, a multimode fiber will be used to replace the single mode fiber 72.

Figure 9A:
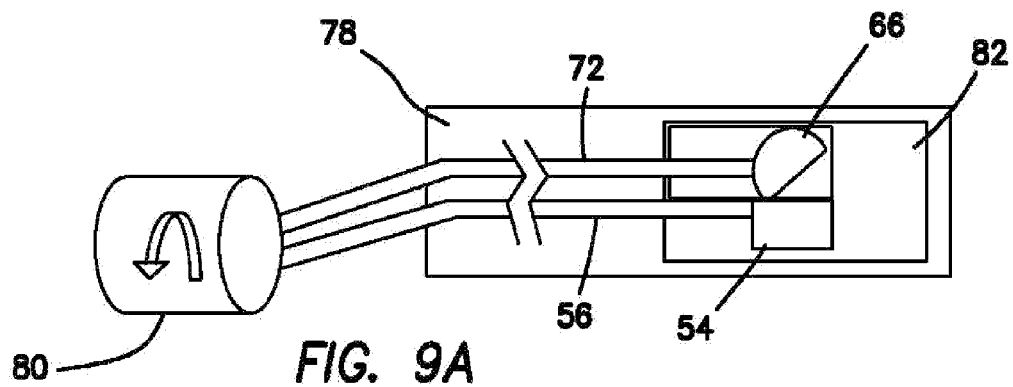
FIG. 9a is a side cross-sectional view of one embodiment of back-to-back integrated probe design by rotating probe proximally and using a ball lens and in FIG. 9b using a GRIN lens for OCT/PA/florescence probe.
Figure 9B:
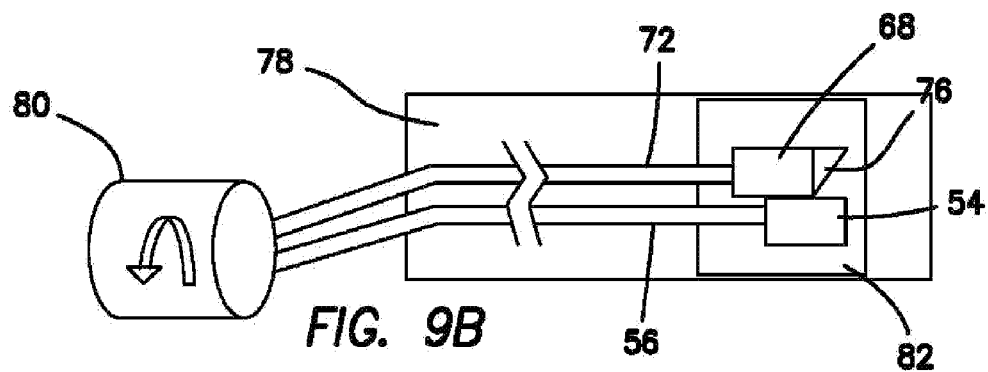

FIGS. 9a and 9b illustrate a cross-sectional view of embodiments of an embodiment using back-to-back integrated catheters 78 for a rotating probe with a ball lens and GRIN lens design respectively. The Ultrasound (US) transducer 54 transmits and receives ultrasound waves used to generate ultrasound images. The optical fiber and ball lens or GRIN lens/prism transmit and receive laser light used to generate OCT images. The torque coil 80 transmits a rotational torque from proximal end to distal end of catheter 78 and ensures a smooth rotation of the catheter shaft. The total diameter of the probe is typically less than 2 mm, and its length is typically greater than 1.5 m. This length is necessary for endoscopic imaging applications because the catheter must pass through the entire accessory channel of the endoscope before it can emerge from the distal end of the endoscope and interface with the tissue. The back-to-back design can significantly reduce the size of the integrated probe and the length of the probe's rigid portion. The reduction in probe size is essential to enable safer and easier delivery through the accessory channel of endoscope, especially to turn, into the bile duct through the sharp turn of the elevator lever mechanism, which directs the catheter out of the accessory channel of the endoscope, during the ERCP procedure With the guidance of visible light from the OCT-subprobe 70 of FIGS. 8*a* and 8*b*, a back-to-back, co-registered OCT-US probe 78 can be made by carefully aligning an OCT subprobe 70 with an US subprobe 52 of FIGS. 7*a* and 7*b*, while confirming that the light beam and sound wave exit at the same axial position, but 180 degrees apart. This integrated probe 78 provides automatically co-registered and co-axial fusion imaging. The combined probe 78 can be then inserted into a customized probe cap 82. Following the probe cap 82, a double wrapped, torque coil 80 to encompass the fiber and electrical, wire, gives the probe 78 adequate flexibility and torque control, in practice, the probe 78 is inserted into a sheath 83. Water or saline is used to fill the sheath 83 and facilitate ultrasound imaging.

Figure 10A:
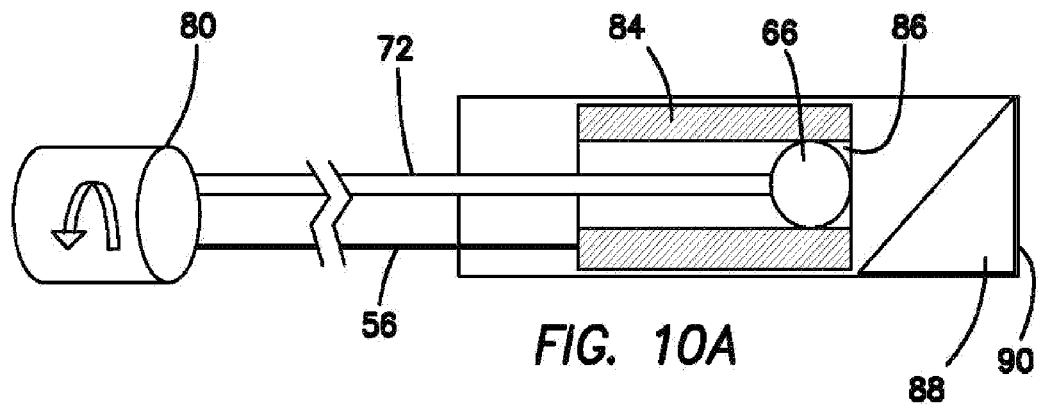
FIG. 10a is a side cross-sectional view of one embodiment of coaxial integrated probe design by rotating probe proximally and using ball lens for OCT/PA/florescence probe and in FIG. 10b using a GRIN lens probe.
Figure 10B:
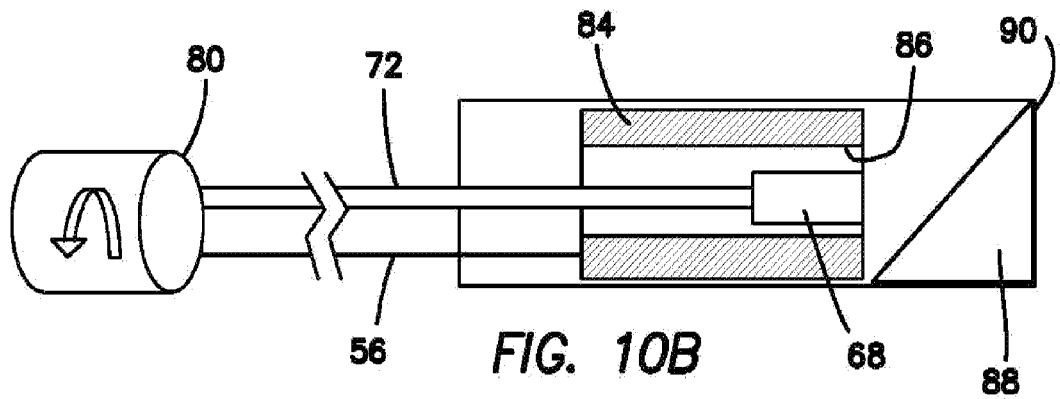

Another embodiment of the invention is shown in FIGS. 10*a* and 10*b* where an ultrasound transducer 84 in a ring shape with the OCT/PA/florescence aperture 86 in the center of the transducer 84 is provided so that both the aperture of transducer 84 and OCT/PA/florescence aperture 86 are concentric with each other and forward facing. The two apertures are forward facing with respect to the longitudinal axis of the probe and in order to directly project and receive both ultrasound and light energy from the tissue surrounding the probe through an angled mirror 88 used to reflect the energy out of and into the ultrasound and OCT/PA/florescence apertures 86. Similar to the back-to-back design of FIGS. 9*a* and 9*b*, the US, OCT, PA and florescence images are automatically registered within the imaging frame. The enlarged ultrasonic transducer 84 of FIGS. 10*a* and 10*b* further increase the penetration depth of US images. The embodiment of FIG. 10*a* uses a ball lens 66 in the OCT/PA/florescence subprobe while the embodiment of FIG. 10*b* uses a GRIN lens 68 in the OCT subprobe. With either of the embodiments of FIGS. 10*a* and 10*b* there most be a sealed barrier, between the rotating probe shaft that contains both the ultrasound and OCT/PA/florescence imaging apertures 86 as well as their corresponding electrical and fiber optic cables. A fluid such as water or saline solution, is provided between the ultrasound and OCT/PA/florescence apertures 86 and a membrane 90 of a protection cap in order to ensure the necessary acoustic impedance matching between the ultrasound transducer 84 and the imaging environment.

Figure 11A:
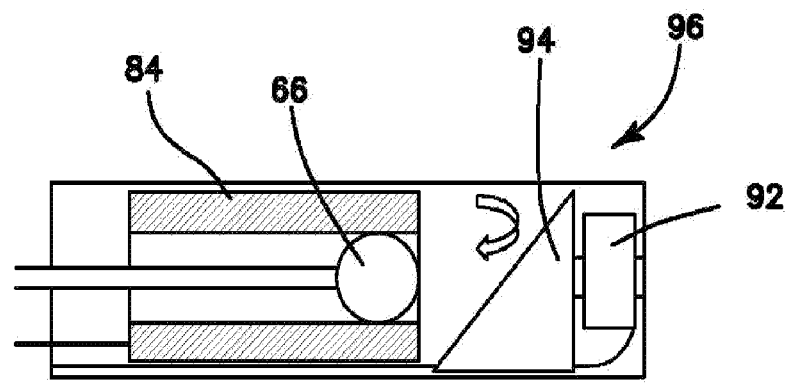
FIG. 11a is a side cross-sectional view of one embodiment of the distal end of the distal-micro-motor-driving OCT/PA/florescence-US probe using a ring transducer and a ball lens or in FIG. 11b using a GRIN lens OCT/PA/florescence probes.
Figure 11B:
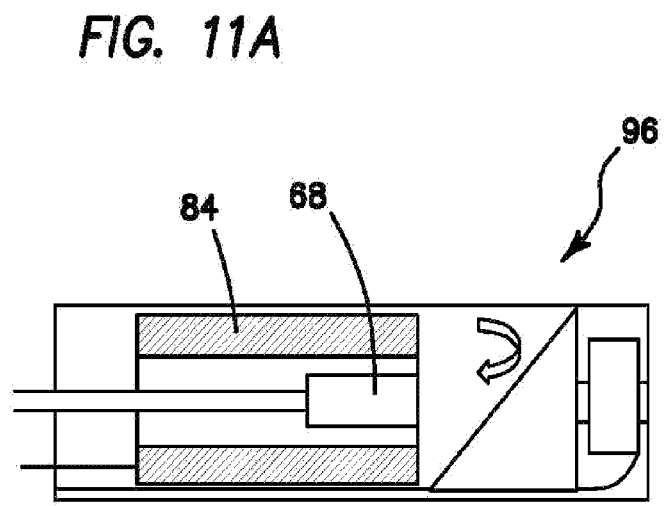

An alternative method of rotating the US and light beams is illustrated in FIGS. 11*a* and 11*b* which uses a micromotor or MEMS motor 92 with mirror 94, which is mounted at the distal tip of an integrated probe 96. The micromotor 92 drives the glass mirror 94 to rate at a speed of 30-500 revolutions per second to scan, the US and OCT/PA/florescence light beams. This design also ensures the automatic and accurate imaging co-registration US and OCT/PA/florescence images. The unique feature of this mirror-rotating design allows a more steady rotation and higher frame rate than the traditional probe-rotating method.

An alternative embodiment uses a circular array transducer (not shown) or ring transducer 84 for side imaging applications in this disclosure. A circular array transducer has the ability to electronically scan the tissue without physically moving an imaging aperture.

Integrated Biopsy Sampling Mechanism

A dual modality imaging catheter may also have an integrated mechanism 98 that has the ability to acquire tissue samples while being used inside the bile duct. The tissue sampling mechanism 98 includes in one embodiment a small hollow-core needle 100 similar to that shown in FIGS. 18*a* and 18*b* that is concealed within the catheter until the physician operates a control to advance the needle 100 forward, exposing it to the surrounding tissue where it can pierce the soft tissue of the bile duct and remove a small piece of tissue and then retract back into the catheter. Once the tissue has been taken from the bile duct and needle 100 is retracted back into the catheter, the catheter can be removed from the accessory port of the endoscope so the tissue sample can be retrieved and analyzed using standard histopathologic methods.

Other features of the catheter may include:

Water Flush—the catheter may have a channel that can be used to flush the bile duct with water so that there is water and not air between the ultrasound transducer and the tissue. This is important because ultrasound waves cannot travel through air without being so highly attenuated that any object beyond the volume of air is impossible to image. Since the water is clear it is not detrimental to the OCT imaging capability of the catheter.

Other tissue sampling mechanism—While the mechanism descripted above uses a hollow core needle 100, other tissue sampling mechanisms may be employed including hollow core needles with the distal tip have a blunt end instead of sharp and pointed (not shown). Small pincers or clamps (not shown) may also be used to grab tissue and tear it from the wall of the GI tract including the bile duct. Tissue may also be drawn inside of the catheter using a vacuum (not shown) and then severed from the surrounding tissue by activating a cutting mechanism (not shown) to remove the desired sample from the surrounding tissue.

Balloon—In order to ensure that the ultrasound transducer is immersed in water, a balloon (not shown) made of latex, low density polyethylene, or some other pliable material could be inflated proximal to the ultrasound transducer and water could then be flushed through a port distal to the balloon so that the water will fill up the bile duct, and be prevented from draining past the balloon, thereby maintaining an acceptable imaging environment for the ultrasound transducer.

Figure 12:
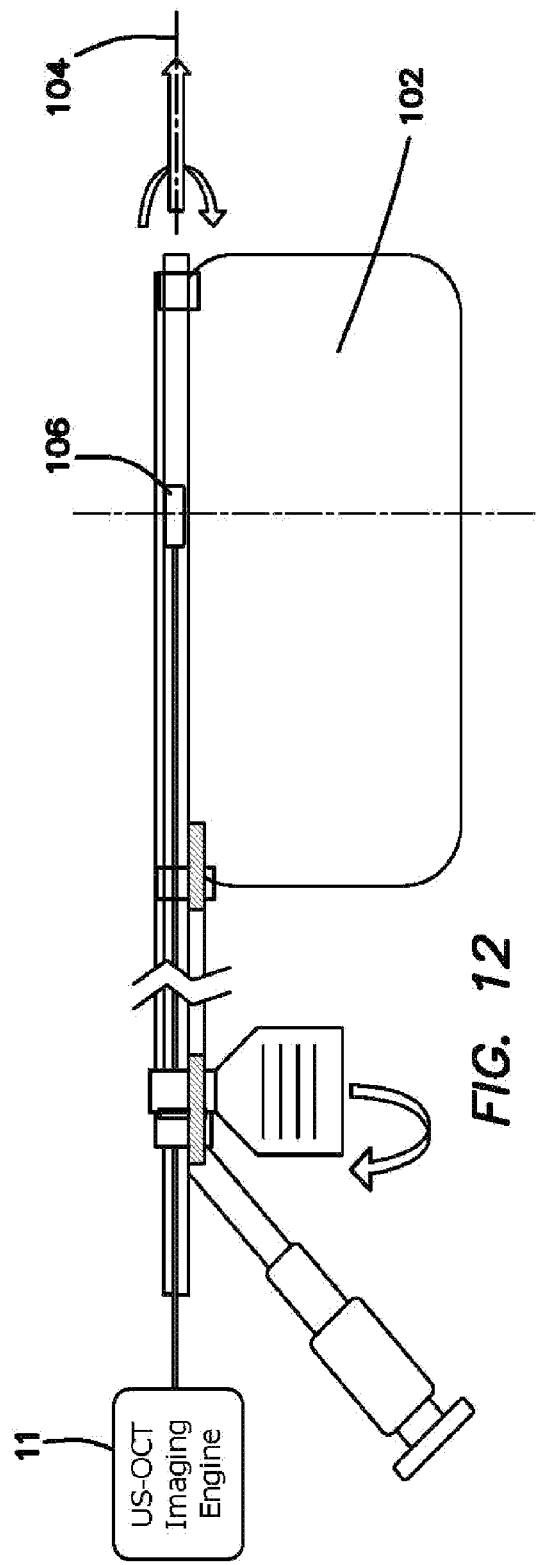
FIG. 12 is a side cross-sectional view of one embodiment of an imaging probe with an asymmetrical water-filled balloon that forces the imaging probe against the inside of the water-filled balloon.
Figure 13B:
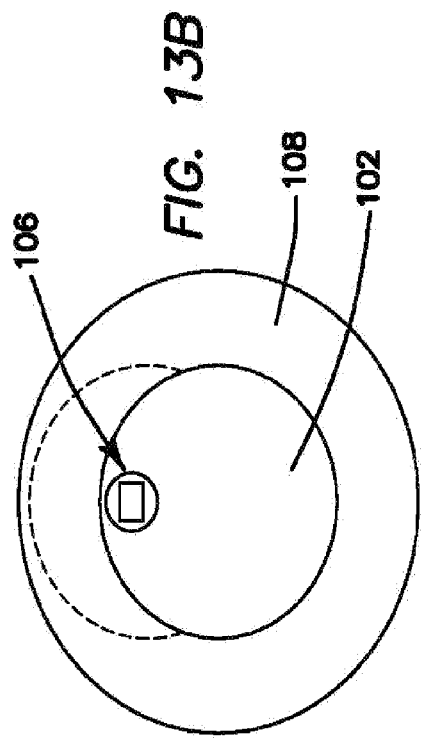
FIGS. 13a and 13b front cross-sectional views of one embodiment of an imaging probe with an asymmetrical, water-filled balloon that forces the imaging probe against the inside of the water-filled balloon.
Figure 13A:
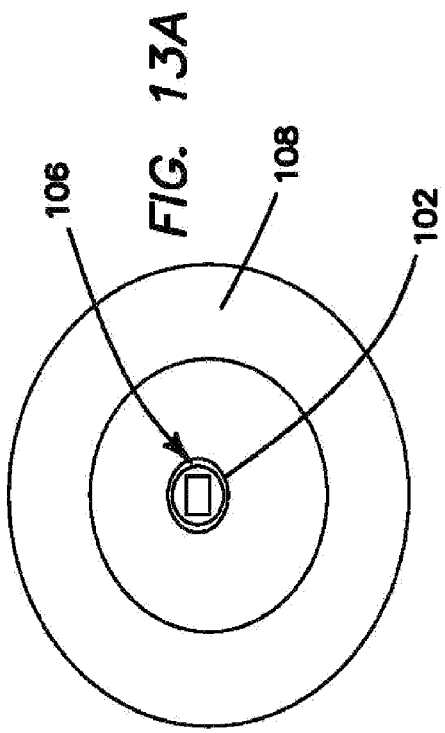

Asymmetrical Balloon-Probe within a Balloon—It may be advantageous to position the probe directly on the lining of the gastrointestinal tract in order to both imaging deeper into the tissue and also to have direct access to the tissue for purposes of collecting a tissue biopsy specimen. In order to reliably press the imaging probe 106 against the lining of the gastrointestinal tract, the probe 106 is integrated within a balloon 102 that when inflated with either water or air is asymmetric in terms of the distance between the outside of the balloon 102 and the center 104 of the imaging probe 106. FIGS. 12, 13*a*, and 13*b* illustrate how the imaging probe 106 rotates freely to acquire images but is forced to be in close proximity to the gastrointestinal wall 108, because of how it is integrated within the balloon 102. Another feature of this design is the ability to rotate the entire balloon 102 with imaging probe 106 located inside, so that the imaging probe 106 directly images all surfaces around the circumference of the gastrointestinal tract 108. This design also allows for the imaging probe 106 to be pulled back and capture multiple imaging slices.

Asymmetrical Balloon-Probe Outside of Balloon—Similar to the embodiment of FIGS. 12, 13a, and 13b, it may be advantageous to position the probe 106 directly on the lining of the gastrointestinal tract 108 in order to both imaging deeper into the tissue and also to have direct access to the tissue for purposes of collecting a tissue biopsy specimen. However, positioning the imaging aperture of the probe 106 outside of the water-filled balloon 102 may be useful as it would remove the necessity for the light and ultrasound energy to travel through the water and wall of the balloon 102. In order to reliably press the imaging probe 106 against the lining of the gastrointestinal tract 108, the probe 106 is attached to the outside of the balloon 102 so that when inflated with, either water or air, the balloon 102 will expand until it contacts the gastrointestinal wall 108 and then press the imaging probe 106 against the opposite side of the gastrointestinal wall 108. FIGS. 14, 15a and 15b show how the imaging probe 106 rotates freely to acquire images, but is forced to be in close proximity to the gastrointestinal wall 108 because of how it is integrated within the balloon 102. Another feature of this design is the ability to rotate the entire balloon 102, with imaging probe 106 located inside, so that the imaging probe 106 directly images all surfaces around the circumference of the gastrointestinal tract 108. This design also allows for the imaging probe 106 to be pulled back, capturing multiple imaging slices and reconstructing a 3D image.

Centering Device for Imaging Probe-Similar to the embodiment of FIGS. 14, 15a and 15b, it may be advantageous to position the probe 106 directly on the lining of the gastrointestinal tract 108 in order to both imaging deeper into the tissue and also to have direct access to the tissue for purposes of collecting a tissue biopsy specimen. Another method of pressing the imaging probe 106 against the wall of the gastrointestinal tract is by inflating a centering balloon 110 within the water-filled balloon 102. This centering balloon 110, shown in FIGS. 16, 17a and 17b, pushes the imaging probe 106 against the wall of the gastrointestinal tract 108. Another feature of this design is the ability to rotate the imaging probe 106 within the water-filled balloon 102 so that the imaging probe 106 directly images all surfaces around the circumference of the gastrointestinal tract 108. An alternative to using a balloon 110 to center the imaging probe 106 is to use a flexible rod (not shown) that when twisted and pushed further into the imaging probe catheter assumes the shape of a coil that expands inside the water filled balloon 102 and forces the imaging probe 106 to the outside of the water filled balloon 102. This flexible rod could be made of a polymer or alloy material and its default shape is straight and compliant enough to bend with the imaging probe 106. This design, also allows for the imaging probe 106 to be pulled back and capture multiple imaging slices.

Vacuum Assist—A channel (not shown) within the catheter could be provided in another embodiment to draw a negative pressure and by placing the output port of the channel next to both of the imaging apertures, the negative pressure causes the bile duct to collapse in towards the catheters and encircle the catheter tightly, ensuring a good seal between the ultrasound transducer and the tissue. Direct, contact between the ultrasound transducer and tissue ensures the ultrasound energy can be sent in and received from the tissue. This also reduces the depth that the ultrasound energy has to travel and enabling for maximum imaging depth without having to move the catheter.

Distal Tip Articulation—It may be useful to articulate the distal tip of the catheter so that it may more easily be navigated into the bile duct or any other part of the gastrointestinal tract.

Guide Wire channel—The probe may have a channel (not shown) that allows a guidewire (not shown) to pass through, it so that during an ERCP, a guidewire is first inserted into the bile duct and then the catheter is subsequently threaded along the guidewire into the place of interest.

Other features of the imaging system may include:

Tissue Sampling Targeting—Display of the tissue biopsy sampling target or needle trajectory on an imaging display during procedure allows the physician to first image the tissue at the time when he or she identifies tissue that he or she deems suspicious and would like to acquire it. Therefore, no guessing or subjective interpretation required to ensure that the tissue is sampled from the intended place.

Distal Tip Biopsy Needle—By integrating the tissue sampling biopsy mechanism 112, shown as a flexible hollow core needle 114 in FIGS. 18a and 18b, in the distal tip of the needle, the size of the catheter can be minimized while still allowing the tissue directly in front of the imaging aperture to be sampled. The biopsy needle 114 is attached to a plunger base 116 that slides along the longitudinal axis of the inner surface of the imaging probe sheath 118. The needle 114 is forced outside of the imaging probe sheath 118 by a ramp or wedge 120 inside the sheath 118. The needle 114 exits the imaging probe sheath 118 through an opening 122. The needle 114 extends enough to pierce the tissue directly in front of the imaging aperture 124. Once the tissue has been captured inside of the hollow core of the needle 114, it is retracted back inside the sheath so that the imaging probe can be withdrawn from the body and the sample collected for analysis such as histopathology imaging.

One implementation of the multiple modality imaging is shown in FIG. 19. The multi-modality imaging system 10 is an integration of a OCT subsystem 130, a fluorescence imaging subsystem 132, an ultrasound imaging subsystem 134, and a photoacoustic imaging subsystem 134. The optical imaging subsystem 138 includes an OCT subsystem 130 and a fluorescence imaging system 132. The US/OCT/florescence system 134 is integrated into a subsystem utilizing common components. The OCT and florescence excitation lasers (not shown) are combined together by a wavelength division multiplexer (WDM) 140. The mixed light wave is coupled into a double-clad fiber (DCF) combiner 142. The single mode core of the DCF is used for OCT signal transmission as well as the fluorescence excitation light delivery. When the light hits the sample and reflects back into the coupler 142, the OCT signal is transmitted through the single mode core and back to the interferometer in subsystem 130. At the same time, fluorescence emission signal is collected by the inner clad of the DCF which has a larger diameter and higher NA; therefore, the efficiency of fluorescence emission light collecting is much higher than the core. The fluorescence signal is coupled through the multimode port of DCF combiner 142 and is detected by a photomultiplier tube in subsystem 132. For the ultrasound part, an ultrasound pulse generator and receiver in subsystem 134 is used for ultrasound signal generation and detection. A trigger from the swept-source laser in subsystem 130 is used to synchronize the optical subsystem 130 and ultrasound subsystem 134. The same trigger is also used for data acquisition. For US/OCT/PA imaging, the OCT and PA excitation lasers in subsystems 130 and 134 are combined together with a wavelength division multiplexer (WDM) 140. The laser induced photoacoustic wave is then detected by the ultrasound transducer in subsystem 134 to generate photoacoustic imaging. A proximal end scanning mechanism 544 is used in this figure, although other scanning mechanisms can also be used. A fiber rotary joint and electrical slip rings are coupled with a rotational motor which rotated the whole multi-modality probe 146. Torque from the motor is translated to the distal end of the probe 146 by a double wrapped torque coil. The rotational system was mounted on a linear stage, which is used for linear translation. The rotational and linear scanning mechanisms 144 allowed the system to provide a three dimensional helical scan. Data acquisition, was carried out by two synchronized data acquisition cards and then processed by a commercial graphical processing unit 148 including display 150. The data processing software of our integrated system 10 was developed to be capable of doing US and OCT/PA/florescence data acquisition, image processing and display in real time.

Image Comparison—The embodiment of the invention records digital images of the tissue and allows digital pathology images of that same tissue to be uploaded and compared to the ultrasound+OCT images so that the physician may be able to learn with each case how the ultrasound+OCT images correspond to the pathology of the tissue. Since the precise location of the tissue biopsy is known and the digital ultrasound+OCT, PA or fluorescence images for that location are also known, precise comparison between the pathology and catheter imaging sets can be performed.

Image Display—The catheter may be connected to a motorized pull-back stage (not shown) so that at the physician's command the system may scan a cross section of the bile duct at many adjacent sections and then reconstruct this imaging data into a useful three dimensional or two dimensional image that the physician may then inspect on a computer monitor at his or her convenience. Once a suspicious lesion is identified within the tissue and is selected with a marking tool that denotes the exact location of the lesion relative to the image, the stage moves the catheter biopsy sampling mechanism to that location and automatically retrieves a tissue biopsy. The system could include many checkpoints throughout this process to ensure that the tissue sample is collected from the right location. One example of this would be for the system to revert back to real-time imaging once the entire section was imaged so that the current, real-time image can be matched to that of the automated pull-back image, ensuring that the biopsy sampling mechanism is in the right location.

In summary, the various embodiments of the invention include:

1. An apparatus comprising a multimodality imaging system including ultrasound, optical coherence tomography (OCT), Photoacoustic (PA) imaging, and/or florescence imaging and endoscopic catheter for imaging inside the gastrointestinal tract with real-time automatic image co-registration capability, including: an ultrasound subsystem for imaging; an optical, coherence tomography (OCT) subsystem for imaging, and PA microscopy or tomography subsystem for imaging and a florescence imaging subsystem for imaging.
  NOTE: The designed OCT fiber and probe is able to incorporate PA imaging and florescence imaging function, thus the terms of OCT subsystem can be referred to OCT/PA/florescence imaging subsystem in this application.
2. The apparatus of paragraph 1 further comprising an invasive interventional imaging device.
3. The apparatus of paragraphs 1 or 2 where the invasive interventional imaging device comprises an instrumentality to take a tissue biopsy from a location visible on the ultrasound subsystem for imaging; optically coherence tomography (OCT) subsystem for imaging, photoacoustic microscopy or tomography subsystem for imaging and/or florescence imaging subsystem for imaging.
4. The apparatus of any of the paragraphs 1-3 where the instrumentality to take a tissue biopsy from a visible location allows simultaneous visualization of the tissue about to biopsied and tissue biopsy with the same instrumentality.
5. The apparatus of any of the paragraphs 1-4 further comprising an endoscope within which the integrated ultrasound, optical coherence tomography (OCT), Photoacoustic (PA) and florescence imaging system and endoscopic catheter are included.
6. The apparatus of any of the paragraphs 1-5 where the endoscopic catheter comprises a balloon-based catheter, and the balloon and imaging sheath material is transparent to ultrasound and OCT/PA/florescence light beam.
7. The apparatus of any of the paragraphs 1-6 where the endoscopic catheter comprises a tethered capsule based catheter, and the imaging channel of the capsule is transparent to ultrasound and OCT/PA/florescence light beam.
8. The apparatus of any of the paragraphs 1-7 where the endoscope comprises an ERCP endoscope and where integrated US and OCT/PA/florescence imaging system comprise a back-to-back ultrasound probe and OCT probe, having rigid components which are miniaturized and having a micromotor, which ultrasound probe and OCT/PA/florescence probe do not require a transition or rotation through a sharp turn.
9. The apparatus of any of the paragraphs 1-8 where the endoscopic catheter comprises a rotational scanning mechanism using a catheter included micromotor.
10. The apparatus of any of the paragraphs 1-9 where the endoscopic catheter comprises a rotational scanning mechanism using a proximal rotation mechanism.
11. The apparatus of any of the paragraphs 1-10 where the optically coherence-tomography (OCT), Photoacousic and florescence subsystem comprises a GRIN lens.
12. The apparatus of any of the paragraphs 1-11 where the optically coherence-tomography (OCT), Photoacousic and florescence subsystem comprises a ball lens.
13. The apparatus of any of the paragraphs 1-12 where the ultrasound subsystem and photoacoustic (PA) subsystems comprise a ring transducer.
14. The apparatus of any of the paragraphs 1-13 where the ultrasound subsystem and photoacoustic (PA) subsystems comprise a single element transducer.
15. The apparatus of any of the paragraphs 1-14 where the ultrasound subsystem for imaging, optical coherence tomography (OCT) subsystem for imaging, PA microscopy or tomography subsystem for imaging and florescence imaging subsystem for imaging, each include a corresponding imaging probe integrated into a system imaging probe and further comprising an asymmetric balloon with the system imaging probe inside or outside of the asymmetric balloon to position the system imaging probe directly on the lining of the gastrointestinal tract.

16. The apparatus of any of the paragraphs 1-15 where the ultrasound subsystem for imaging, optical coherence tomography (OCT) subsystem for imaging, PA microscopy or tomography subsystem for imaging and florescence imaging subsystem for imaging, each include a corresponding imaging probe integrated into a system imaging probe and further comprising an asymmetric balloon with a centering balloon disposed therein, the system imaging probe being disposed inside of the asymmetric balloon and positioned by the centering balloon directly adjacent to the lining of the gastrointestinal tract.

17. The apparatus of any of the paragraphs 1-16 where the ultrasound subsystem includes an ultrasound transducer and further comprising a vacuum assist to draw adjacent tissue and the ultrasound transducer together into contact.

18. The apparatus of any of the paragraphs 1-17 further comprising a distal tip articulation of the endoscopic catheter, and a guidewire channel defined in the endoscopic catheter or other mechanism to navigate the endoscopic catheter to a location of interest for imaging.

19. The apparatus of any of the paragraphs 1-18 further comprising a distal end biopsy needle included in the endoscopic catheter.

20. A method comprising imaging tissue in the gastrointestinal tract using invasive interventional imaging device which includes an integrated ultrasound, optical coherence tomography (OCT), Photoacoustic (PA) and florescence imaging system; and taking a biopsy from an imaged location in the gastrointestinal tract using the invasive interventional imaging device, while simultaneously imaging the imaged location.

21. The method of paragraph 20 further comprising using an endoscopic catheter to position the integrated ultrasound, optical coherence tomography (OCT), Photoacoustic (PA) and florescence imaging system in the gastrointestinal tract.

22. The method of paragraphs 20 or 21 where using the endoscopic catheter comprises using a balloon-based catheter to position, the integrated ultrasound, optical coherence tomography (OCT), Photoacoustic (PA) and florescence imaging system in the gastrointestinal tract.

23. The method of any of the paragraphs 20-22 where the endoscopic catheter comprises using a tethered capsule based catheter to position the integrated ultrasound, optical coherence tomography (OCT), Photoacoustic (PA) and florescence imaging system in the gastrointestinal tract.

24. The method of any of the paragraphs 20-23 where during an endoscopic-retrograde cholangiopancreatography procedure (ERCP) using the endoscopic catheter comprises using a back-to-back ultrasound probe and OCT probe in the integrated ultrasound, optical coherence tomography (OCT), Photoacoustic (PA) and/or florescence imaging system, which probes have rigid components which are miniaturized and have a micromotor, which ultrasound probe and optical coherence tomography (OCT), Photoacoustic (PA) and/or florescence probe do not require a transition or rotation through a sharp turn.

25. The method of any of the paragraphs 20-24 where the integrated ultrasound, optical coherence tomography (OCT), Photoacoustic (PA) and/or florescence imaging system includes a system imaging probe and further comprising using an asymmetric balloon with the system imaging probe inside or outside of the asymmetric balloon to position the system imaging probe directly on the lining of the gastrointestinal tract.

26. The method of any of the paragraphs 20-25 where the integrated ultrasound, optical coherence tomography (OCT), Photoacoustic (PA) and/or florescence imaging system includes a system imaging probe and further comprising using an asymmetric balloon with a centering balloon disposed therein, disposing the system, imaging probe inside of the asymmetric balloon and positioning the system imaging probe by means of the centering balloon to position the system imaging probe directly adjacent to the lining of the gastrointestinal tract.

27. The method of any of the paragraphs 20-26 further comprising drawing adjacent tissue by means of a vacuum assist into contact with an ultrasound transducer.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification are approximate, not exact. They are intended to have a reasonable range which is consistent with the functions to which they relate and with what is customary in the art to which they pertain.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed, in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

The use of this invention will be not limited to the GI tract cancer imaging and diagnosis. The integrated US, OCT, PA or florescence endoscopic imaging system can be also used in other endoscopic imaging applications, such as the imaging of respiration system for diagnosing lung/bronchus cancer, nasal/sinus cancer and larynx cancer with same imaging mechanism.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined, to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An apparatus comprising:
   an integrated multimodality imaging system for ultrasound, optical coherence tomography (OCT), photoacoustic (PA) imaging, florescence imaging;
   an invasive interventional imaging device; and
   an endoscopic catheter in which the integrated multimodality imaging system is disposed for imaging inside the gastrointestinal tract with real-time automatic multimodal image co-registration,
   wherein the integrated multimodality imaging system includes:
      an ultrasound subsystem for imaging;
      an optical coherence tomography (OCT) subsystem for imaging;
      PA microscopy or tomography subsystem for imaging; and
      a florescence imaging subsystem for imaging, and
   wherein the invasive interventional imaging device comprises:
      a biopsy needle within the endoscopic catheter orientated to obtain a tissue sample from a location of the gastrointestinal tract being concurrently viewed by the integrated multimodality imaging system.

2. The apparatus of claim 1 wherein the biopsy needle of the invasive interventional imaging device is disposed distally within the endoscopic catheter relative to the integrated multimodality imaging system.

3. The apparatus of claim 1 wherein the endoscopic catheter has an adjustable length to enable imaging of different locations within the GI tract including esophagus, stomach, duodenum, bile duct, pancreatic duct, colon, small intestine or rectum.

4. The apparatus of claim 2 wherein the invasive imaging device further comprises a wedge, wherein the biopsy needle orientated to obtain a tissue sample from a location of the gastrointestinal tract being viewed by the integrated multimodality imaging system is configured to interact with the wedge to take a tissue biopsy from a location visible on the integrated multimodality imaging system.

5. The apparatus of claim 4 wherein the integrated multimodality imaging system is configured to simultaneously visualize the tissue about to biopsied and the tissue biopsy.

6. The apparatus of claim 1 further comprising an endoscope within which the integrated ultrasound, optical coherence tomography (OCT), photoacoustic (PA) and florescence imaging subsystems and endoscopic catheter are included.

7. The apparatus of claim 1 where the endoscopic catheter comprises a balloon configured to press the integrated multimodality imaging system against a surface of the gastrointestinal tract.

8. The apparatus of claim 1 where the endoscopic catheter comprises a tethered capsule based catheter.

9. The apparatus of claim 6 where the endoscope comprises an ERCP endoscope and where integrated ultrasound-optical coherence tomography (OCT)/photoacoustic (PA)/florescence imaging system comprise a back-to-back ultrasound probe and OCT/PA/florescence probe, having rigid components which are miniaturized and having a micromotor, which ultrasound probe and OCT/florescence probe do not require a transition or rotation through a sharp turn.

10. The apparatus of claim 1 where the endoscopic catheter comprises a rotational scanning mechanism using a catheter included micromotor.

11. The apparatus of claim 1 where the endoscopic catheter comprises a rotational scanning mechanism using a proximal rotation mechanism.

12. The apparatus of claim 1 where the optical coherence tomography (OCT)/photoacoustic (PA)/florescence subsystems comprise a GRIN lens.

13. The apparatus of claim 1 where the optical coherence tomography (OCT)/photoacoustic (PA)/florescence subsystem comprises a ball lens.

14. The apparatus of claim 1 where the ultrasound subsystem comprises a ring transducer for generating ultrasound image and photoacoustic (PA) image.

15. The apparatus of claim 1 where the ultrasound subsystem comprises a single element transducer made of PMN-PT 1-3 composite material.

16. The apparatus of claim 1 where the ultrasound subsystem for imaging, and the optical coherence tomography (OCT), photoacoustic (PA) imaging, florescence subsystem for imaging and endoscopic catheter for imaging each include a corresponding imaging probe integrated into a system imaging probe and further comprising an asymmetric balloon with the system imaging probe inside or outside of the asymmetric balloon to position the system imaging probe directly on the lining of the gastrointestinal tract.

17. The apparatus of claim 1 where the ultrasound subsystem for imaging, and the optical coherence tomography (OCT), photoacoustic (PA) imaging, florescence subsystem for imaging and endoscopic catheter for imaging each include a corresponding imaging probe integrated into a system imaging probe and further comprising an asymmetric balloon with a centering balloon disposed therein, the system imaging probe being disposed inside of the asymmetric balloon and positioned by the centering balloon directly adjacent to the lining of the gastrointestinal tract.

18. The apparatus of claim 1 where the ultrasound subsystem includes an ultrasound transducer and further comprising a vacuum assist to draw adjacent tissue and the ultrasound transducer together into contact.

19. The apparatus of claim 1 further comprising a distal tip articulation of the endoscopic catheter, and a guidewire channel defined in the endoscopic, catheter or other mechanism to navigate the endoscopic catheter to a location of interest for imaging.

20. A method comprising:
 imaging tissue in the gastrointestinal tract using an invasive interventional imaging device which includes an integrated multimodality imaging system including ultrasound for imaging, optical coherence tomography (OCT), photoacoustic (PA) imaging, florescence imaging and endoscopic catheter for imaging; and
 taking a biopsy from an imaged location in the gastrointestinal tract using a biopsy needle disposed within the invasive interventional imaging device, while simultaneously imaging the imaged location using the integrated multimodality imaging system.

21. The method of claim 20 further comprising using an endoscopic catheter to position the integrated multimodality imaging system in the gastrointestinal tract.

22. The method of claim 21 where using the endoscopic catheter comprises using a balloon-based catheter to position the integrated multimodality imaging system against a surface of the gastrointestinal tract.

23. The method of claim 21 where using the endoscopic catheter comprises using a tethered capsule based catheter to position the integrated multimodality imaging system in the gastrointestinal tract.

24. The method of claim 21 where during an endoscopic retrograde cholangiopancreatography procedure (ERCP) using the endoscopic catheter comprises using a back-to-back ultrasound probe and OCT probe in the integrated multimodality imaging system, which probes have rigid components which are miniaturized and have a micromotor, which ultrasound probe and OCT probe do not require a transition or rotation through a sharp turn.

25. The method of claim 20 further comprising using an asymmetric balloon with a system imaging probe within the integrated multimodality imaging system inside or outside of the asymmetric balloon to position the system imaging probe directly on the lining of the gastrointestinal tract.

26. The method of claim 20 further comprising using an asymmetric balloon with a centering balloon disposed therein, disposing a system imaging probe within the integrated multimodality imaging system inside of the asymmetric balloon and positioning the system imaging probe by means of the centering balloon to position the system imaging probe directly adjacent to the lining of the gastrointestinal tract.

27. The method of claim 20 further comprising drawing adjacent tissue by means of a vacuum assist into contact with an ultrasound transducer.

* * * * *